US007728490B2

(12) United States Patent
Adachi et al.

(10) Patent No.: US 7,728,490 B2
(45) Date of Patent: Jun. 1, 2010

(54) CAPACITIVE MICROMACHINED ULTRASONIC TRANSDUCER

(75) Inventors: Hideo Adachi, Iruma (JP); Etsuko Omura, Iruma (JP); Akiko Mizunuma, Hachioji (JP); Katsuhiro Wakabayashi, Hachioji (JP); Takuya Imahashi, Kawasaki (JP); Yukihiko Sawada, Tokorozawa (JP); Shuji Otani, Ome (JP); Miyuki Murakami, Hino (JP); Kiyoshi Nemoto, Hino (JP); Kozaburo Suzuki, Hachioji (JP); Naomi Shimoda, Kodaira (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/606,881

(22) Filed: Nov. 30, 2006

(65) Prior Publication Data

US 2007/0164631 A1 Jul. 19, 2007

Related U.S. Application Data

(63) Continuation of application No. PCT/JP2005/010410, filed on Jun. 7, 2005.

(30) Foreign Application Priority Data

Jun. 7, 2004 (JP) ............................. 2004-168672
Jun. 8, 2004 (JP) ............................. 2004-169658

(51) Int. Cl.
*H04R 17/00* (2006.01)

(52) U.S. Cl. ....................................... 310/334; 310/311

(58) Field of Classification Search .................. 310/334
See application file for complete search history.

(56) References Cited

U.S. PATENT DOCUMENTS 5,287,331 A * 2/1994 Schindel et al. ............. 367/140
7,275,298 B2 * 10/2007 Schindel ....................... 29/594
2005/0075572 A1 * 4/2005 Mills et al. .................. 600/459
2005/0146247 A1 * 7/2005 Fisher et al. ................ 310/334
2006/0170014 A1 * 8/2006 Smith et al. ................. 257/252

FOREIGN PATENT DOCUMENTS

JP 63-237700 10/1988
JP 07-107595 4/1995
JP 08-080300 3/1996
JP 2003-299195 10/2003
JP 3478874 10/2003
WO WO 03/035281 A2 5/2003

OTHER PUBLICATIONS

Igal Ladabaum et al., "Surface Mircomachined Capacitive Ultrasonic Transducers", IEEE Transaction on Ultrasonics, Ferroelectrics, Anifrequencv Controm, May 1998, vol. 45,No. 3, pp. 678to 690.

* cited by examiner

*Primary Examiner*—Walter Benson
*Assistant Examiner*—Bryan P Gordon
(74) *Attorney, Agent, or Firm*—Scully, Scott, Murphy & Presser, P.C.

(57) ABSTRACT

A capacitive micromachined ultrasonic transducer having an ultrasonic wave transmission/reception surface formed by arranging a plurality of transducer cells each of which includes a membrane having a first electrode and a supporting film for supporting the first electrode, and also includes a second electrode arranged being opposite to the first electrode and being spaced apart from the first electrode at a prescribed interval, wherein: the transducer cells are arranged on the basis of resonant frequencies of the transducer cells.

4 Claims, 27 Drawing Sheets

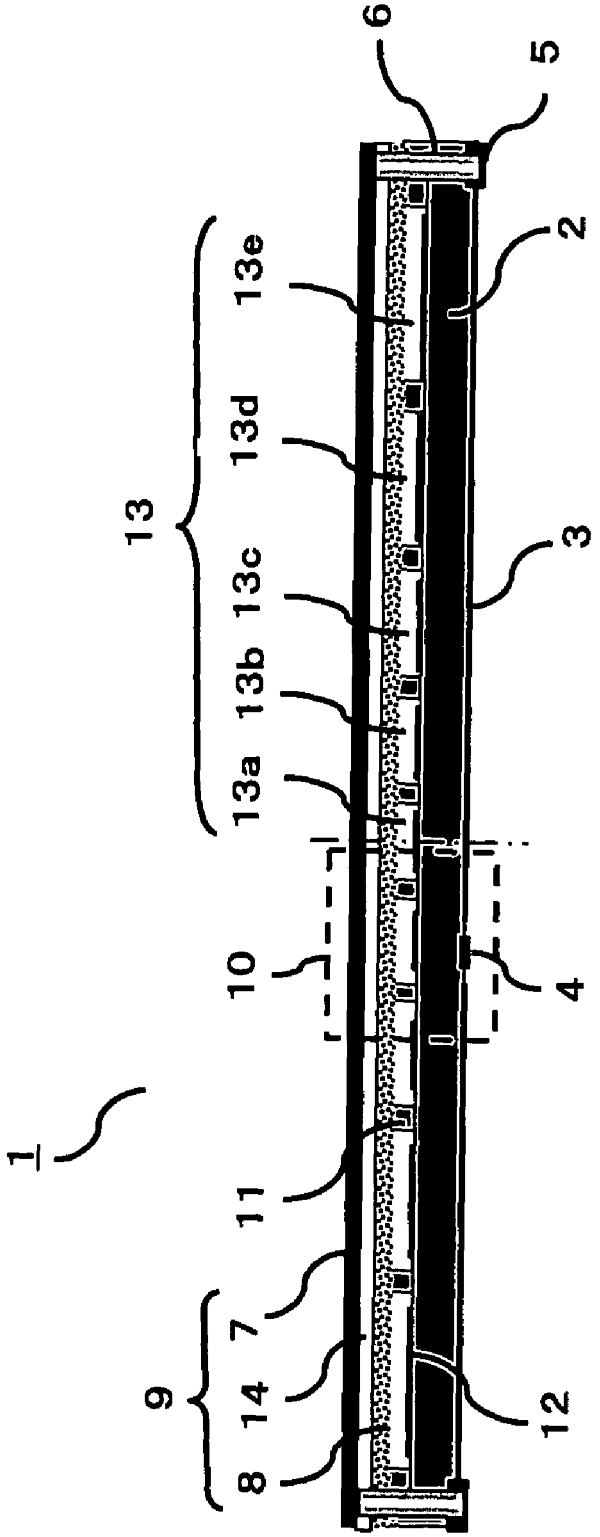
F I G. 1

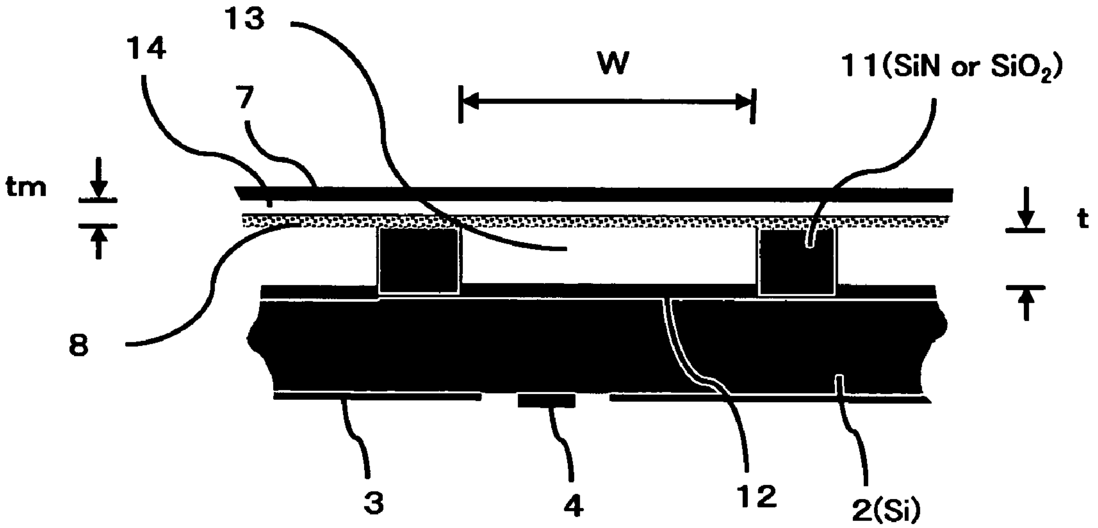
F I G. 2

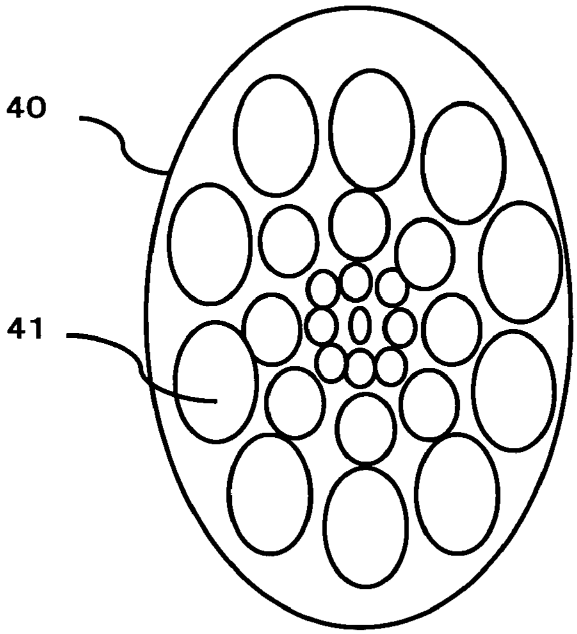
FIG. 5A
FIG. 5B
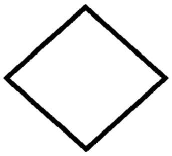
FIG. 5C
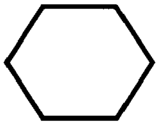
FIG. 5D
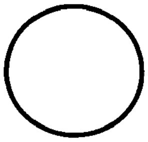

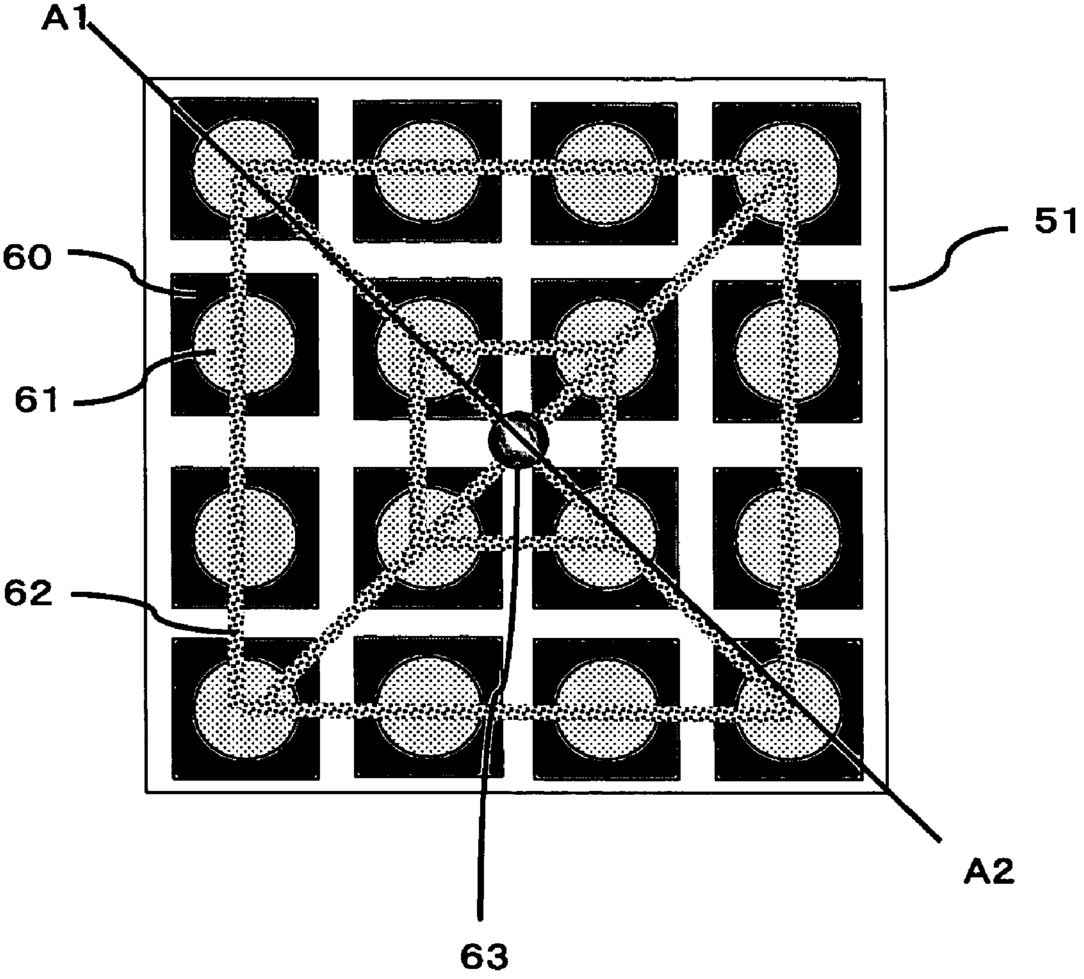
F I G. 7

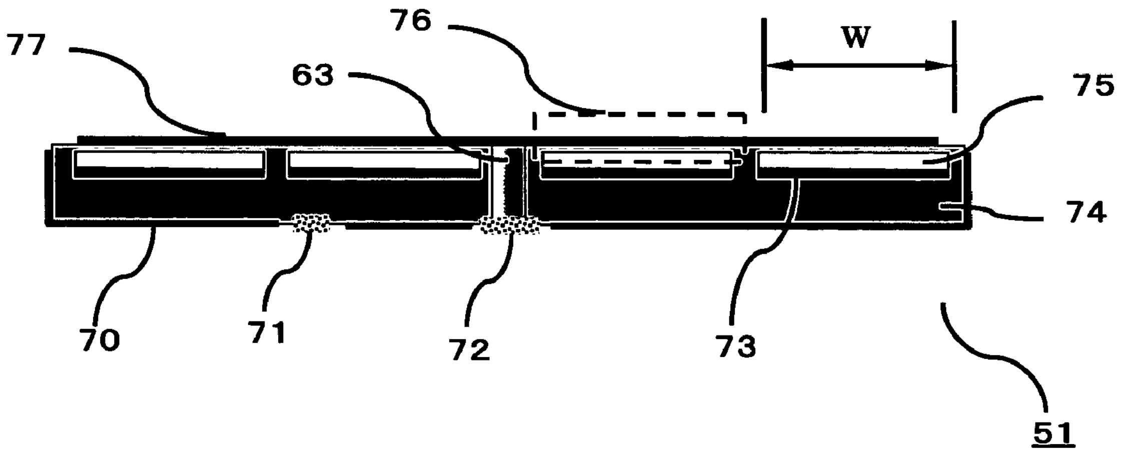
F I G. 8

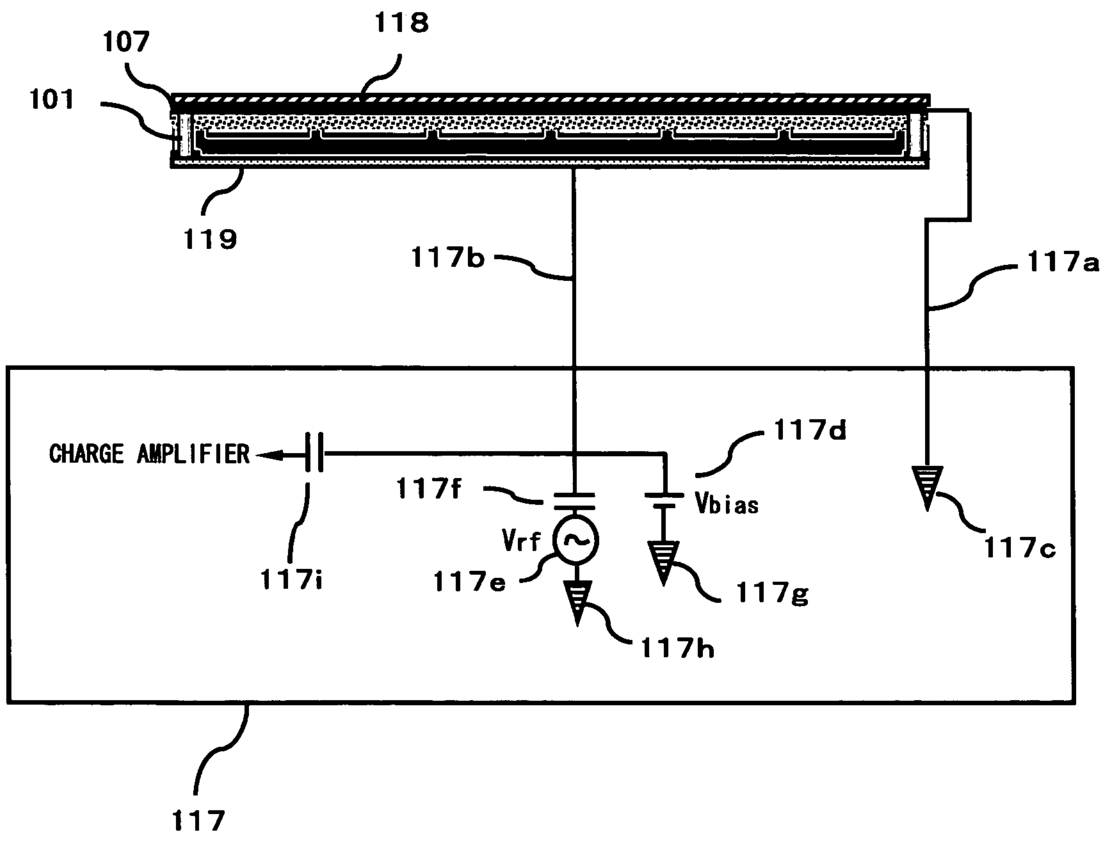
F I G. 10

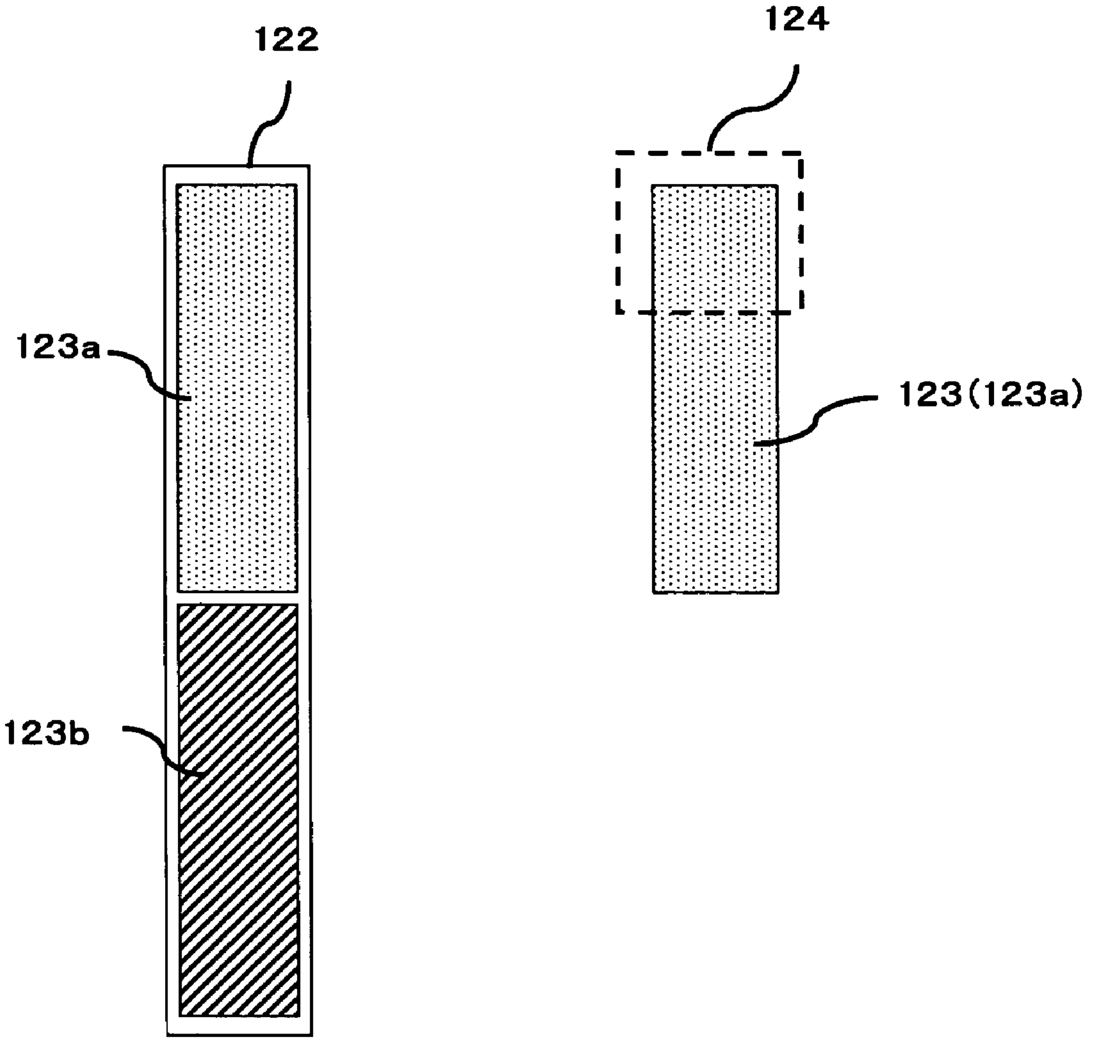
F I G. 1 2

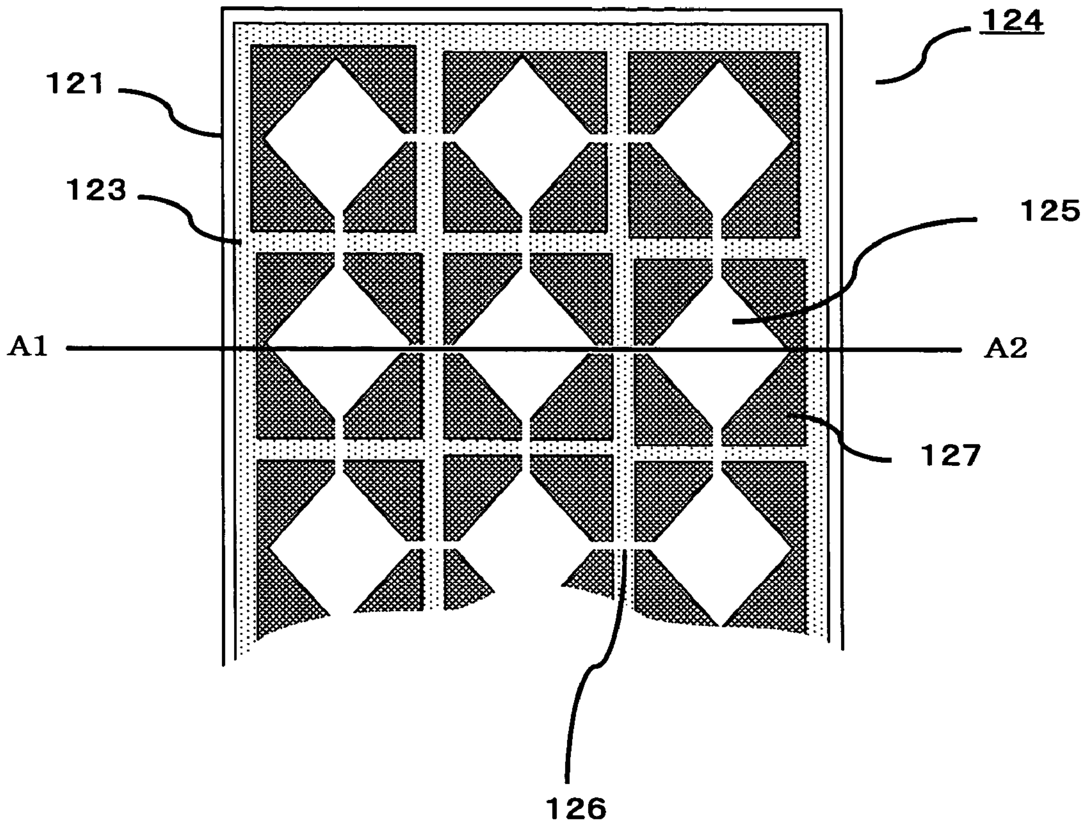
F I G. 1 3

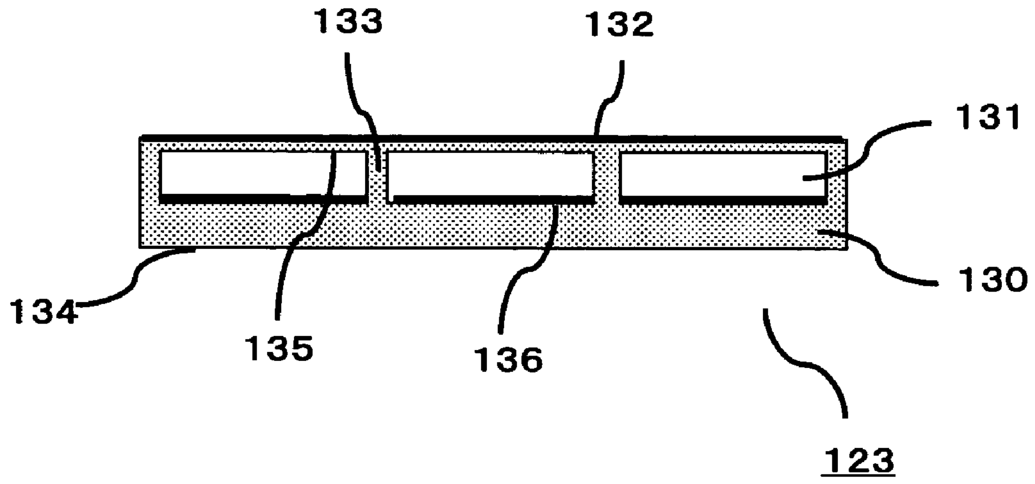
F I G. 1 4

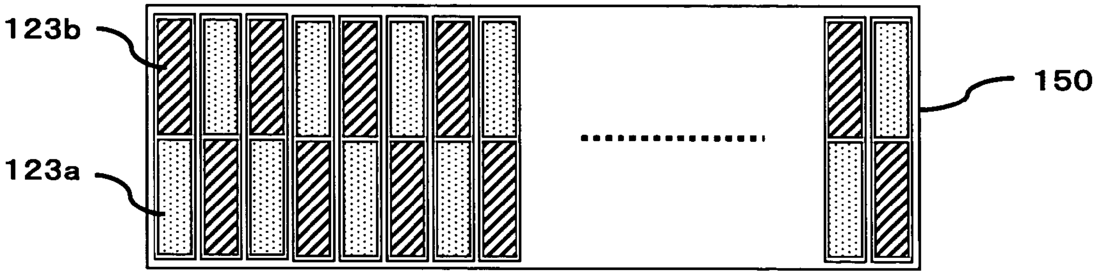
F I G. 1 6

CAPACITIVE MICROMACHINED ULTRASONIC TRANSDUCER

CROSS REFERENCE TO RELATED APPLICATIONS

This is a Continuation Application of PCT Application No. PCT/JP2005/010410 filed, filed Jun. 7, 2005, which was not published under PCT Article 21(2) in English.

This application is based upon and claims the benefit of priority from the prior Japanese Patent Application No. 2004-168672 filed in Japan on Jun. 7, 2004, the entire contents of which are incorporated herein by reference.

This application is based upon and claims the benefit of priority from the prior Japanese Patent Application No. 2004-169658 filed in Japan on Jun. 8, 2004, the entire contents of which are incorporated herein by reference.

BACKGROUND OF THE INVENTION

1. Field of the Invention

The present invention relates to a capacitive micromachined ultrasonic transducer.

2. Description of the Related Art

Ultrasonic diagnosis methods in which ultrasonic waves are transmitted inside a body cavity are widely employed and the condition of the body cavity is visualized on the basis of the echo signals. An ultrasonic endoscope is one device used for ultrasonic diagnosis. In an ultrasonic endoscope, an ultrasonic transducer is provided to the distal end of an insertion unit, which is inserted into body cavities. This transducer converts electric signals into ultrasonic waves for transmitting them inside body cavities, and also receives reflected ultrasonic waves in the body cavities in order to convert them into electric signals.

Some ultrasonic transducers have a configuration including, for example, a circular and concave ultrasonic reflection plane and a planar back plane, i.e., a plano-concave configuration (see, for example, Japanese Patent Application Publication No. 2003-299195 and Japanese Patent No. 3478874). In the concave ultrasonic reflection plate, the central spot has the minimum thickness, and the closer to the periphery a spot is, the greater the thickness of the spot is.

A piezoelectric element is included in an ultrasonic transducer, which converts ultrasonic waves and electric signals into each other. The piezoelectric element generates ultrasonic waves at different frequencies in accordance with the thickness of respective portions in the element itself. Specifically, ultrasonic waves at low frequencies are generated at portions having a great thickness, and ultrasonic waves at high frequencies are generated at portions having a small thickness because ultrasonic wave frequency is in inverse proportion to the thickness of the piezoelectric element.

Therefore, in an ultrasonic transducer having a circular and concave ultrasonic reflection plate i.e., in an ultrasonic transducer having the plano-concave configuration, the ultrasonic wave at the highest frequency is generated at the central spot, and the closer to the periphery a spot is, the lower the frequency of the wave transmitted from the spot is.

The purpose of generating ultrasonic waves at different frequencies as above is to obtain images at different resolutions based on the different frequencies. By using ultrasonic waves at high frequencies, image information of the surface and around it can be obtained at a high resolution. However, ultrasonic waves at high frequencies are subjected to attenuation at deeper portions. When ultrasonic waves at low frequencies are used, the resolution of image information is lower than that of the image information obtained by using the ultrasonic waves at high frequencies. However, the ultrasonic waves at low frequencies are less subjected to the attenuation, and can therefore be used for observation of deeper portions. Accordingly, by synthesizing the ultrasonic waves at high frequencies and the ultrasonic waves at low frequencies, it is possible to obtain ultrasonic images of shallower to deeper portions at relatively high resolution.

Additionally, for ultrasonic image processing methods and ultrasonic image processing apparatuses using parametric sound source methods, an ultrasonic image processing apparatus using the parametric array has been disclosed in recent years, in which the attenuation of echo signals can be reduced (see, for example, Japanese Patent Application Publication No. 8-80300).

Japanese Patent Application Publication No. 8-80300 discloses the following method. By transmitting from an ultrasonic probe to a sample of an amplitude-modulated wave whose center frequency is amplitude-modulated or an ultrasonic wave having two frequency components, an echo having a frequency component of a difference that is based on the nonlinearity of tissues is generated in the sample. Because the echo having the frequency component of the difference is lower than the fundamental frequency, the attenuation of the signal strength while the wave is being transmitted through the sample becomes much smaller.

The parametric array used herein is a sound source whose beam pattern is sharper than that of a wave at a frequency that is the same as that of a difference tone between waves at different frequencies. An effect that results from the acoustic characteristic (parametric characteristic) achieved by this parametric array is called a parametric effect.

Recently, capacitive micromachined ultrasonic transducers (referred to as c-MUT hereinafter) have been attracting interest. The capacitive micromachined ultrasonic transducer is one of several devices that are categorized into MEMS (Micro Electro-Mechanical Systems).

A MEMS device is a device that is formed as a microstructure on a substrate such as a silicon substrate, a glass substrate, or the like. In a MEMS device, driven bodies for outputting mechanical forces, driving mechanisms for driving the driven bodies, semiconductor integrated circuits for controlling the driving mechanisms, and the like are electrically and mechanically connected. A MEMS device is mainly characterized by the configuration in which the driven bodies that are configured as mechanisms are incorporated into the device. The driven bodies are electrically driven by using the Coulomb attraction between electrodes.

A capacitive micromachined ultrasonic transducer (c-MUT) is a device in which two planar electrodes are arranged such that they face each other, having a cavity between the electrodes. The capacitive micromachined ultrasonic transducer transmits ultrasonic waves when it receives AC signals superposed on a DC bias by having a layer (membrane) including one of the above electrodes oscillate harmonically to the AC signals received.

SUMMARY OF THE INVENTION

In the capacitive micromachined ultrasonic transducer according to the present invention having an ultrasonic wave transmission/reception surface formed by arranging a plurality of transducer cells each of which includes a membrane having a first electrode and a supporting film for supporting the first electrode, and also includes a second electrode arranged being opposite to the first electrode and being spaced apart from the first electrode at a prescribed interval:

the transducer cells are arranged on the basis of resonant frequencies of the transducer cells.

Additionally, in the capacitive micromachined ultrasonic transducer according to the present invention in which a plurality of transducer elements are arranged, each having a plurality of transducer cells each of which includes a membrane having a first electrode and a supporting film for supporting the first electrode, and also includes a second electrode arranged being opposite to the first electrode and being spaced apart from the first electrode at a prescribed interval:

the transducer elements are arranged on the basis of the frequencies of ultrasonic waves transmitted from the transducer elements.

Additionally, in the capacitive micromachined ultrasonic transducer according to the present invention having a plurality of transducer elements each including a plurality of transducer subelements each having a plurality of transducer cells each of which includes a membrane having a first electrode and a supporting film for supporting the first electrode, and also includes a second electrode arranged being opposite to the first electrode and being spaced apart from the first electrode at a prescribed interval:

each of the transducer subelements is any one of a first transducer subelement and a second transducer subelement respectively transmitting ultrasonic waves having frequency components different from each other;

the transducer cells in the transducer subelements have the same resonant frequency; and an ultrasonic wave transmission/reception surface is formed by arranging the transducer elements.

Additionally, in the capacitive micromachined ultrasonic transducer according to the present invention including a plurality of transducer elements each having a plurality of transducer cells each of which includes a membrane having a first electrode and a supporting film for supporting the first electrode, and also includes a second electrode arranged opposite to the first electrode and spaced apart from the first electrode at a prescribed interval:

each of the transducer elements includes the first transducer cell and the second transducer cell that transmit ultrasonic waves respectively having frequency components different from each other;

the ultrasonic wave transmitted from each of the transducer elements is a difference frequency ultrasonic wave based on the ultrasonic wave transmitted from the first transducer cell and the second transducer cell; and the waves are converged such that the difference frequency ultrasonic waves are put in focus by controlling the driving timing of the respective transducer elements.

Additionally, in the capacitive micromachined ultrasonic transducer according to the present invention having a plurality of transducer cells each of which includes a membrane having a first electrode and a supporting film for supporting the first electrode, and also includes a second electrode arranged being opposite to the first electrode and being spaced apart from the first electrode at a prescribed interval:

each of the transducer cells is any one of a first transducer cell and a second transducer cell respectively transmitting ultrasonic waves having frequency components different from each other;

the first transducer cell and the second transducer cell have resonant frequencies that are different from each other; and an ultrasonic wave transmission/reception surface is formed by arranging the first transducer cell and the second transducer cell in an alternating series.

Additionally, in the capacitive micromachined ultrasonic transducer according to the present invention having a plurality of transducer cells each of which includes a membrane having a first electrode and a supporting film for supporting the first electrode, and also includes a second electrode arranged being opposite to the first electrode and being spaced apart from the first electrode at a prescribed interval:

the capacitive micromachined ultrasonic transducer includes an ultrasonic wave transmission/reception surface in which at least three types of transducer cells respectively transmitting ultrasonic waves having different frequency components are arranged such that a difference frequency ultrasonic wave based on the ultrasonic waves transmitted from the respective transducer cells is generated.

Additionally, in the capacitive micromachined ultrasonic transducer according to the present invention having a plurality of transducer elements each including a plurality of transducer subelements each having a plurality of transducer cells each of which includes a membrane having a first electrode and a supporting film for supporting the first electrode, and also includes a second electrode arranged being opposite to the first electrode and being spaced apart from the first electrode at a prescribed interval:

the capacitive micromachined ultrasonic transducer includes an ultrasonic wave transmission/reception surface in which at least three types of the transducer subelements respectively transmitting ultrasonic waves having different frequency components are arranged such that a difference frequency ultrasonic wave based on the ultrasonic waves transmitted from the respective transducer subelements is generated.

BRIEF DESCRIPTION OF THE DRAWINGS

FIG. 1 shows a basic configuration of a capacitive micromachined ultrasonic transducer according to the first embodiment;

FIG. 2 is an enlarged view of a portion 10 enclosed by the dashed line in FIG. 1;

FIGS. 5A-5D show an example of variations of shapes of cells in the second embodiment;

FIG. 7 shows an upper face of an element 51 according to the third embodiment;

FIG. 8 shows a cross section of the element shown in FIG. 7 across the line A1-A2;

FIG. 10 shows a driving unit of the c-MUT according to the fourth embodiment;

FIG. 12 shows an element and a subelement of a capacitive micromachined ultrasonic transducer according to the fourth embodiment;

FIG. 13 is an enlarged view of a part (part 124 enclosed by the dashed line) of a subelement 123;

FIG. 14 shows a cross section of the subelement 123 shown in FIG. 13 across the line A1-A2;

FIG. 16 shows the first example of a unit 140 of a capacitive micromachined ultrasonic transducer according to the fifth embodiment;

DESCRIPTION OF THE PREFERRED EMBODIMENTS

First Embodiment

Figure 3A:
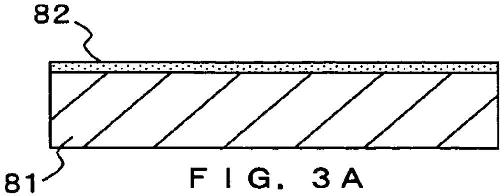
FIGS. 3A-3I show a manufacturing method of an ultrasonic transducer element 1 according to the first embodiment.

In the present embodiment, a capacitive micromachined ultrasonic transducer is explained. In this capacitive micromachined ultrasonic transducer, high-frequency waves are transmitted from the central spot, and the closer to the circumference the spot from which waves are transmitted is, the lower the frequency of the transmitted waves.

FIG. 1 shows a basic configuration of a capacitive micromachined ultrasonic transducer (c-MUT) according to the present embodiment in a cross-sectional view. The unit of the c-MUT shown in FIG. 1 is referred to as an transducer element 1 (simply referred to as an element, hereinafter) The c-MUT includes a plurality of recesses on the surface of a silicon substrate 2. This unit is referred to as an transducer cell 10 (simply referred to as a cell, hereinafter). A membrane 9 is set on the upper face of the silicon substrate 2 such that the respective cells 10 are covered.

The membrane 9 is an oscillation film whose end portions are fixed with membrane supporting parts 11. The membrane 9 is made of a thin film containing an upper electrode 7, a membrane bottom film 14, and a highly dielectric oxide layer 8. The membrane bottom film 14 is used for supporting the upper electrode. It should be noted that the highly dielectric oxide layer 8 may be used as the membrane bottom film 14.

On the lower face of the silicon substrate 2, an insulation film 3 is provided. On a part of the insulation film 3, a lower-face electrode pad (a contact pad) 4 is arranged. Interconnects via holes 6 are provided at both ends of the silicon substrate 2. A contact pad 5 is arranged on one end (on the lower-face side of the silicon substrate) of each interconnect via a hole.

FIG. 2 is an enlarged view of the portion enclosed by a dashed line in FIG. 1. One element is constituted by a plurality of cells. The membrane 9 is supported by the membrane supporting parts 11 located at both sides of the cells 10.

The lower electrodes 12 are arranged on the surfaces (the bottom part of the recesses) between the membrane supporting parts 11 on the silicon substrate 2. The cavity 13 is space enclosed by the membrane 9, the membrane supporting parts 11, and the lower electrode 12. The width of the cavity (or electrode) is represented by W, the thickness of the membrane 9 is represented by tm, and the interval between the upper electrode 7 and the lower electrode 12 is represented by t. The width of the membrane corresponding to the above width of the cavity is also referred to as membrane width.

The configuration of the capacitive micromachined ultrasonic transducer is further explained by referring to FIG. 1 and FIG. 2. First, an etching process is executed on the surface of the silicon substrate 2 for forming a plurality of recesses. Specifically, a pattern of material that serves as the membrane supporting parts 11 such as SiN (silicon nitride) is formed on the silicon substrate 2 by using a conventional film forming method, and a plurality of recesses are formed. It should be noted that the material of the membrane supporting parts 11 does not necessarily have to be SiN, and it can be any material that is a highly insulative, such as $SiO_2$ or the like.

The respective recesses are partitioned by the membrane supporting parts 11. On the bottom of each of these recesses, the lower electrode 12 is arranged. The interconnects via holes 6 are conductive channels piercing the silicon substrate 2 from its upper face to its lower face.

The cavities 13*a*-13*e*, collectively referenced with reference numeral 13, are formed by using a sacrificial layer etching method, and the membrane supporting parts 11 are made of insulating material such as SiN, $SiO_2$ or the like. This forming method will be explained later by referring to FIGS. 3A-3I.

The contact pad 5 is arranged on an end (on the lower-face side of the silicon substrate 2) of each interconnect via hole 6. The contact pads 5 serve as terminals on the lower face side of the silicon substrate 2 for the connection to the upper electrode 7.

The insulation film 3 (for example, $SiO_2$) is formed on the lower face of the silicon substrate 2, and the contact pad 4 is arranged on a part of the insulation film 3. This contact pad 4 serves as a conduction terminal for the lower electrodes 12. Because the silicon substrate 2 is made of silicon material having a low resistance value, the conduction with the lower electrodes 12 is realized through this contact pad 4.

The insulation film 3 serves as an insulator between the contact pad 4 and the contact pads 5. After the junction, voltage can be applied from the lower face of the silicon substrate 2 to the upper electrode 7 and the lower electrodes 12 respectively through the contact pad 4 and the contact pads 5.

In the above configuration, the upper electrode 7 is conductive to the contact pads 5 (pad electrodes) via the interconnect via holes 6 for each element, but is insulated from the silicon substrate 2 having a low resistance. The lower electrodes 12 and the contact pad 4 are conductive to each other via the silicon substrate 2 having a low resistance, and thus the above contact pads are insulated from each other so that a signal short circuit does not happen between them.

It should be noted that the contact pads 4 and 5 are arranged such that they can be jointed to input/output units (contact pads) of a pulsar circuit or a charge amplifier circuit as integrated circuits by using a solder bump or the like.

Figure 3B:
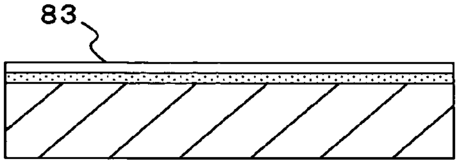

FIG. 3A-3I shows a manufacturing method for the ultrasonic transducer element 1 according to the present embodiment. As shown in FIG. 3A, an insulating layer 82 of $SiO_2$, SiN or the like is formed on the upper face of the silicon substrate 81. This film may be a highly dielectric film. Next, as shown in FIG. 3B, a lower electrode 83 is formed on this insulating layer 82.

Figure 3C:
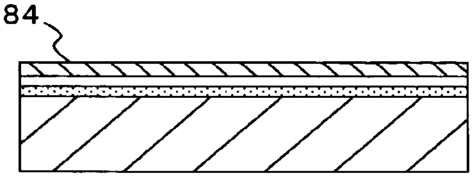

Next, as shown in FIG. 3C, a sacrificial layer 84 is formed, and this layer is sacrificed for forming cavities or the like (in other words, it is a temporary layer that will be removed in a later stage). This sacrificial layer 84 can be formed using, for example, polysilicon that can be easily removed.

Figure 3D:
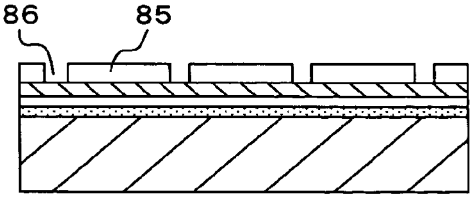

Next, as shown in FIG. 3D, masks (resist films) 85 are formed two-dimensionally on the portions that will define cavities on the sacrificial layer 84. In FIG. 3A-I, a cross section in a horizontal direction is shown; however, the masks 85 are formed similarly also in the vertical direction.

In peripheral portions (portions that will serve as membrane supporting parts) 86 of the respective cavities, the mask 85 is not formed.

Figure 3E:
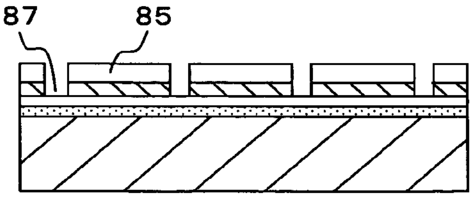

Next, as shown in FIG. 3E, the portions on the sacrificial layer 84 which are not masked by the masks 85 are removed through an etching process in order to form recess portions 87 used for forming the membrane supporting parts.

Figure 3F:
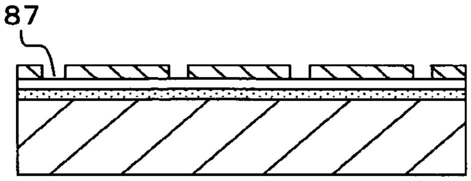
Figure 3G:
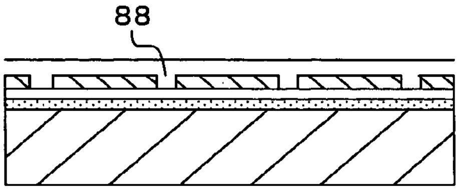

Next, as shown in FIG. 3F, the masks 85 are removed. It should be noted that the peripheral portions 86 and the recess portion 87 will serve as posts. Then, as shown in FIG. 3G, the recess portions 87 are filled in order to form the membrane supporting parts. Also, a film 88 is formed by using a membrane substrate (SiN, $SiO_2$ or the like) such that the film 88 covers the upper faces of the sacrificial layer 84.

Figure 3H:
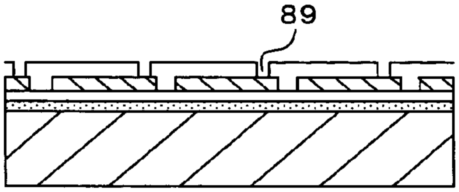
Figure 3I:
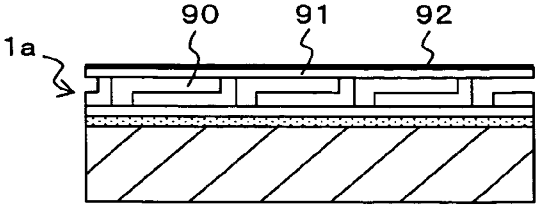

Next, as shown in FIG. 3H, sacrificial layer escape holes 89 which extend to the sacrificial layer 84 under the film 88 are made. Then, the sacrificial layer 84 is removed by etching or the like. Then, cavities 90 are formed after the removal of the sacrificial layer 84. A membrane layer (sacrificial layer escape hole sealing film) 91 is formed in order to cover the hole 69. This membrane layer 91 may be made of SiN or $SiO_2$. This film may be a highly dielectric film. FIG. 3I shows the state that exists when an upper electrode 92 is formed on the membrane layer 91.

By executing the steps shown in FIG. 3A through FIG. 3I, the steps shown in FIG. 3C through FIG. 3I are repeated on an ultrasonic transducer element 1*a* as the first layer. Thereby, an ultrasonic transducer element 1*b* (not shown) can be formed as the second layer.

Next, operations of a c-MUT 1 will be explained. When voltage is applied to the upper electrode 7 and the lower electrode 12, these electrodes attract each other, and when the voltage becomes zero, they attraction stops. Ultrasonic waves are generated by this oscillation, and the ultrasonic waves are transmitted upward from the upper electrode.

As shown in FIG. 1, in the present embodiment the respective cells have different widths. The element shown in FIG. 1 has a configuration that is symmetrical with a dashed line at the middle of the view that represents the line of symmetry. Also, the closer to the ends a cell is, the larger the width of the cell. Accordingly, the membrane width W satisfies the relationship of 10*a*<10*b*<10*c*<10*d*<10*e*. This will be explained below.

The center frequency fres of the ultrasonic wave generated from each cell is expressed by equation (1) below.

$$fres=(\pi/2)\times(tm/W^2)\times(E/12\rho)^{1/2} \quad (1)$$

(tm: thickness of membrane, W: membrane width, E: Young's modulus, ρ: density)

Accordingly, the greater the membrane width W is, the smaller fres. In other words, the greater the membrane width per one cell, the lower the frequency. Accordingly, when the membrane width W per one cell is gradually increased such that the relationship of 10*a*<10*b*<10*c*<10*d*<10*e* is satisfied, the central cell generates the ultrasonic wave whose center frequency fres is the highest (high frequency), and the closer to the ends a cell is, the smaller the central frequency of the ultrasonic wave (low frequency) generated by the cell. It should be noted that fres may be adjusted by changing the thickness of the membrane.

Also, by forming the highly dielectric oxide layer 8 on the upper electrode 7, it is possible to enhance the strength of the ultrasonic waves generated by the cells. The highly dielectric oxide layer 8 is a layer that is formed to enhance the electrostatic attraction between the upper electrode 7 and the lower electrodes 12. The voltage applied to the upper electrode 7 and the lower electrodes 12 is controlled such that the upper electrode 7 and the lower electrodes 12 are oscillated, and there by ultrasonic waves are generated. Accordingly, the stronger the electrostatic attraction between the upper electrode 7 and the lower electrodes 12, the more they are oscillated. Accordingly, methods of enhancing the electrostatic attraction are described. Equation (2) below expresses the electrostatic attraction Fatt between the upper electrode 7 and each of the lower electrodes 12.

$$Fatt=-(1/2)\times\in_r\times(W^2/t^2)\times V^2 \quad (2)$$

($\in_r$: dielectric constant, W: membrane width, t: interval between electrodes, V: voltage)

The above equation expresses the fact that the greater the dielectric constant is, the stronger the electrostatic attraction Fatt between electrodes if t, $W^2$, and V are constant. Accordingly, by interposing material having a great dielectric constant between the upper electrode 7 and the lower electrode 12, it is possible to make the electrostatic attraction Fatt stronger. The highly dielectric oxide layer 8 serves as this material interposed between the upper electrode 7 and the lower electrode 12.

Accordingly, material having a large dielectric constant is used for the highly dielectric oxide layer 8. In the present embodiment, as the highly dielectric oxide layer 8, material having a large dielectric constant is used, such as Barium Titanate $BaTiO_3$ ($\in_r$: 1200), Strontium Titanate $SrTiO_3$ ($\in_r$: 332), Barium Strontium Titanate, Tantalum oxide ($\in_r$: 27.9), Tantalum (V) oxide ($\in_r$: 27), NST ($\in_r$: 27), Aluminum oxide, Titanium oxide ($\in_r$: 100), or the like.

Further, the element is explained. The respective cells in the element have a resonant frequency. The resonant frequency depends on equation (1), i.e., it depends on structural parameters. At the resonant frequency, an oscillation amplitude that is larger than that at other frequencies is realized.

Thus, from the central spot of the element, a high-frequency ultrasonic wave is transmitted, and the closer to the ends a spot transmitting an ultrasonic wave is, the lower the frequency of the ultrasonic wave transmitted from the spot. In the present invention, these ultrasonic waves at different frequencies are caused to be in focus, which will be explained by referring to FIG. 4.

Figure 4:
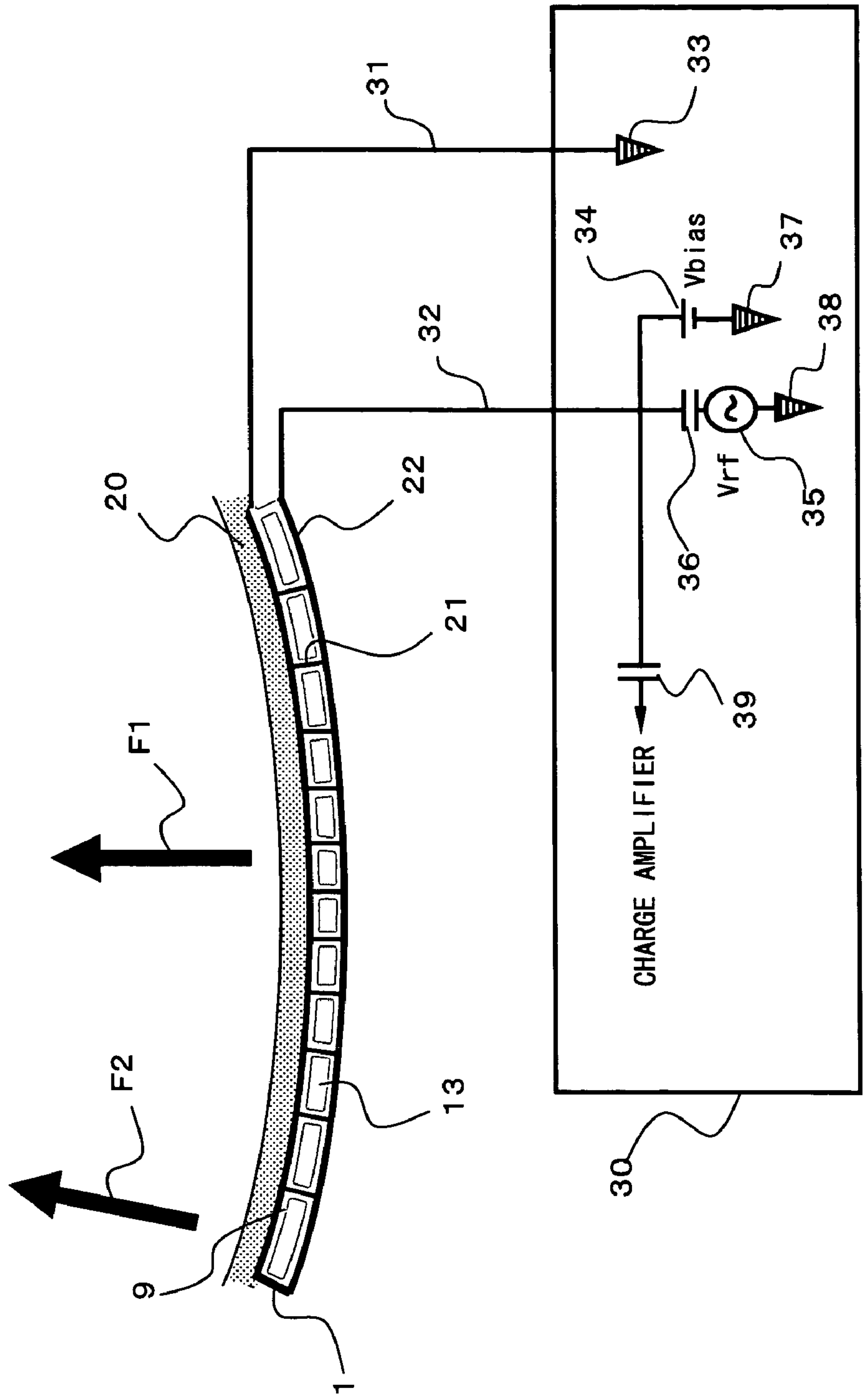
FIG. 4 shows a configuration in which the element in FIG. 1 is curved so that the ultrasonic waves transmitted from the entire surface of the element are in focus.

FIG. 4 shows a configuration in which the element in FIG. 1 is curved so that the ultrasonic waves transmitted from the entire surface of the element are in focus. First, a flexible printed circuit (FPC) 20 is jointed to the surface of the membrane 9 of the element 1 in FIG. 1. Next, in order to curve the element 1 via a mechanical operation as shown in FIG. 4, slits are formed from the insulation film 3 to the membrane supporting parts 11 for each space between the cells before the curvature process. Then, each cell is partitioned from its adjacent cell such that it is supported by the membrane 9. Thereby, the element can be curved easily.

Next, as shown in FIG. 4, the element is curved such that the central portion is in a concave state. When the element is curved, the focal length is set in advance, and the curvature is conducted such that the ultrasonic waves transmitted from the surface of the element are in focus at the set focal length. After the curvature process, in order to maintain the curved state of the element, the grooves formed due to the above slits are filled with back-filling agent 21. Thereafter, on the surface on which the slits were made (insulation film 3), lower-face electrodes 22 are formed. Thereby, the curved state as shown in FIG. 4 is realized.

Next, operations of the c-MUT shown in FIG. 4 will be explained. The driving unit 30 is a device for driving the c-MUT, and includes ground wiring 31, signal wiring 32, grounds 33, 37, and 38, a DC bias power source 34, an RF power source 35, and DC blocking capacitors 36 and 39.

The upper electrode 7 is grounded at the ground 33 via the ground wiring 31. The signal wiring 32 is for transmitting driving signals generated by the driving unit to the c-MUT1.

The RF power source 35 is a high-frequency alternating current source for generating the driving signals. To generate the driving signal, not only alternating voltage components ($V_{rf}$) supplied from the RF power source 35, but also direct voltage components ($V_{bias}$) supplied from the DC bias power source 34 are necessary. The driving signals thus generated are transmitted to the lower-face electrode 22 via the DC blocking capacitor 36 and the signal wiring 32. One terminal of the DC bias power source 34 is grounded at ground 37, and one terminal of the RF power source 35 is grounded at ground 38.

The DC blocking capacitors 36 and 39 are for preventing direct current of the DC bias power source 34 from flowing into a charge amplifier or into the RF power source 35.

When the driving unit 30 is driven, the driving signal is transmitted to the c-MUT and the membrane of each cell oscillates such that an ultrasonic wave is transmitted from each cell. As shown in FIG. 4, ultrasonic wave F1 at a high frequency is transmitted from the central cell of the c-MUT, and ultrasonic waves F2 at low frequencies are transmitted from the cells around the central cells. These ultrasonic beams are in focus at the center of the circle that is constituted by the surface of this c-MUT.

By thus constituting the focus as above, it is possible to diaphragm the width of the ultrasonic beam. Because the width of the ultrasonic beam influences the spatial resolution of an ultrasonic image, it is desirable that the beam width be diaphragmed as much as possible without causing a problem in the depth of the ultrasonic wave.

Also, by curving the surface of the c-MUT as above, a functionality equivalent to that realized by the above described plano-concave configuration can be realized. The plano-concave configuration is characterized in that it transmits high-frequency ultrasonic signals from its central spot, transmits low-frequency ultrasonic signals from the peripheral spots, and forms a sound field in which a synthesized sound field of the high-frequency ultrasonic waves and the low-frequency ultrasonic waves is constant across the distance from near portions (high frequency) to far portions (low frequency). Because low-frequency ultrasonic signals have a high sensitivity, it is possible to cause an ultrasonic wave to travel for a long distance, i.e., to a deeper portion.

The reason that the high-frequency components influence near sound fields is that the high-frequency ultrasonic wave is transmitted from the central spot such that the aperture is small and waves are in focus at a near position. The reason that the low-frequency components influence far sound fields is that the low-frequency ultrasonic waves are transmitted from peripheral spots such that the aperture is substantially larger, and the waves are in focus at a far position. Therefore, the c-MUT in the present embodiment has the functionality as above.

In the present embodiment, the resonant frequency that a plurality of transducer cells have are distributed over a plurality of frequency bands. The phrase "distributed over a plurality of frequency bands" means that in the transducer element in the present embodiment, the peripheral spots are for the low frequency (band), and the central spots are for the high frequency (band), i.e., a plurality of frequencies are distributed over the element. In this configuration, the driving signals having the same frequency band are applied to the transducer elements at that resonant frequency. Thereby, it is possible to efficiently transmit ultrasonic beams from the respective cells distributed over the element.

As the structural parameters that determine the resonant frequency of the cell, the membrane width and the length/diameter (in the case that the cell is circular) are employed on the basis of the principle expressed by equation (1). It should be noted that in the present embodiment, the transmission/reception surface of the capacitive micromachined ultrasonic transducer is concave, and the concave surface may be spherical or cylindrical. Also, in the present embodiment a high-frequency wave is an ultrasonic wave at a frequency which is relatively higher than the frequencies of other ultrasonic waves (low frequency), and a low-frequency wave is an ultrasonic wave at a frequency which is relatively lower than the frequencies of other ultrasonic waves (high frequency).

Conventionally, in an ultrasonic transducer, a ceramic piezoelectric material, PZT (Lead Titanate Zirconate) for example, is used as a piezoelectric element for converting electrical signals into ultrasonic waves. However, it is difficult to process this material into the plano-concave configuration, and it is further difficult to arrange electrodes on it in a curved state. However, with the configuration in which the capacitive micromachined ultrasonic transducer is curved and an ultrasonic wave at a high frequency is transmitted from the central spot of the element, and the closer to the ends of the element a spot is, the lower the frequency of the ultrasonic waves transmitted from the spot is, an ultrasonic image at relatively high resolution from near portions to far portions can be obtained.

Also, the functions that are conventionally realized by using the plano-concave configuration can be realized easily. Further, the capacitive micromachined ultrasonic transducer according to the present embodiment can be manufactured more easily than a conventional transducer manufactured by processing a piezoelectric element into a plano-concave configuration.

Second Embodiment

In the present embodiment, cells having apertures in various shapes are formed in elements, and high-frequency waves are transmitted from the central spot of the element and low-frequency waves are transmitted from the spots around the central spot.

FIG. 5A-5D shows the upper face of an element according to the present embodiment. FIG. 5A shows an element 40 in an oval shape in which a plurality of cells 41 in an oval shape are formed. The central cell has the smallest area, and the closer to the periphery of the element a cell is, the larger the area of the cell.

As described above, by changing the membrane width W, the frequency can be changed to being in inverse proportion to $W^2$ (see equation (1)). Thus, when a cell having a small area at the central point of the element is formed and when other cells are arranged such that the closer to the periphery of the element a cell is, the larger the area of the cell, high-frequency waves are transmitted from the central spots, and the closer to the periphery a cell is, the lower the frequency of the wave transmitted from the spot.

FIGS. 5B, 5C, and 5D show examples of variations in cell shapes. In FIG. 5A, an oval cell is used; however, the present invention is not limited to this example. Specifically, the shapes of cells may be quadrangular (FIG. 5B), hexagonal (FIG. 5C) (a honeycomb structure for example), or circular (FIG. 5D). Further, the shapes of the element are not limited to being oval, and may be quadrangular, hexagonal, or circular.

By arranging the cells in concentric circles (or concentric ovals) such that the closer to the periphery a cell is, the larger the area of the cell, the central spot of the element transmits a high frequency wave, and the closer to the periphery a spot is, the lower the frequency of an ultrasonic wave transmitted from the spot. Thus, an ultrasonic image at a resolution that is relatively high over the distance from near portions to far portions can be obtained.

Third Embodiment

In the present embodiment, a capacitive micromachined ultrasonic transducer is realized in which a plurality of elements are arranged such that the central element transmits a high-frequency wave, and the further an element is from the central element, the lower the frequency of waves transmitted from the element, and in which the same effect as that of the first embodiment is achieved by an electric control without physically curving the ultrasonic wave transmission/reception surface.

Figure 6:
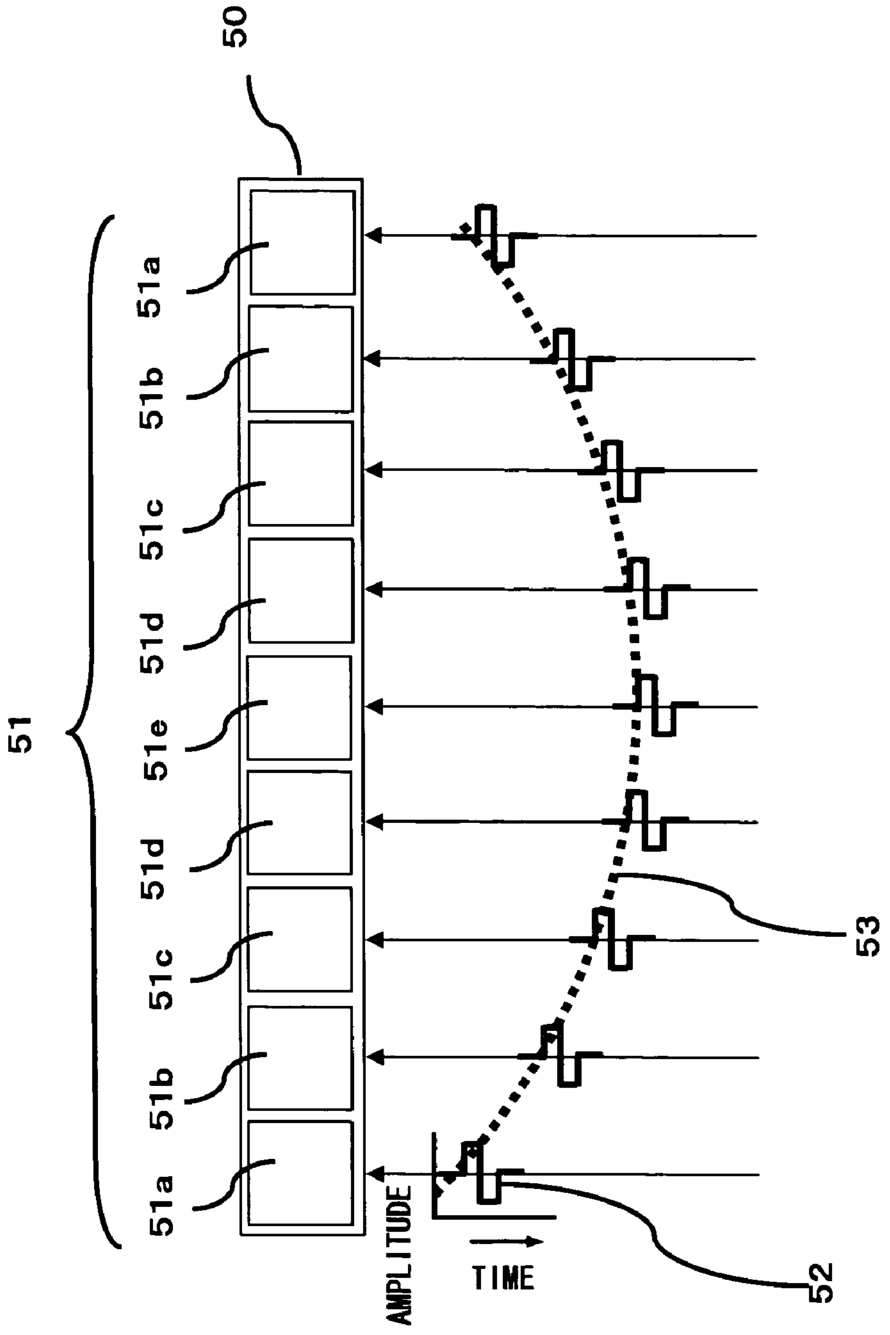
FIG. 6 shows the timing of inputting driving pulses into a unit and respective elements of a capacitive micromachined ultrasonic transducer in the third embodiment.

FIG. 6 shows a unit of the capacitive micromachined ultrasonic transducer according to the present embodiment. On a substrate 54, a plurality of elements 51 (nine elements, 51*a*, 51*b*, 51*c*, 51*d*, 51*e*, 51*d*, 51*c*, 51*b*, and 51*a*) are arranged. In this embodiment, this group of elements 51 is referred to as a unit 50.

FIG. 7 shows the upper face of the element 51 according to the present embodiment. In the element 51, sixteen (four× four) cells 60 are arranged in a square shape. Because these cells have the same configuration, ultrasonic waves at the same frequency are transmitted. At the center of the upper face of each cell 60, an upper electrode 61 is arranged. Each upper electrode 61 is connected to the upper electrodes 61 on its adjacent cells via interconnect electrodes 62. At the central spot of the element 51, an interconnect via hole 63 is formed.

FIG. 8 shows a cross section of the element shown in FIG. 7 across the line A1-A2. In FIG. 8, the cross section of the element 51 includes an insulation film 70, contact pad electrodes 71 and 72, lower electrodes 73, a silicon substrate 74, cavities 75, and a membrane 76.

The membrane 76 includes an upper electrode 77, and a membrane bottom film (a highly dielectric material may also be included). The upper electrode 77 includes an upper electrode 61 on each cell and an interconnect electrode 62. The width of the cavity 75 (width of the electrode in units of cells) is represented by W. The functions of these members are the same as those in the first embodiment.

By referring to FIG. 6 again, operations of the unit 50 realized in the present embodiment will be explained. First, a driving pulse 52 is input into each element. Although a pulse on which a DC pulse is superimposed is used as the driving pulse 52, only RF pulses before the superimposition are shown in FIG. 6. In FIG. 6, the driving pulses 52 represent the amplitudes with respect to the time. A delay time is given to the driving pulse input into each element, and these driving pulses are input in the order of 51*a*, 51*b*, 51*c*, 51*d*, and 51*e* at prescribed intervals. Also, each element includes the driving unit explained in FIG. 4, and the driving pulse is input into this driving unit. The driving pulse is transmitted from a control unit in an ultrasonic endoscope apparatus (not shown).

Inputting the driving pulses into the element with delay times causes the ultrasonic waves to be transmitted from the element with time gaps. Specifically, the element 51*a* that is driven earlier transmits the ultrasonic wave earlier, and because the elements 51*b*, 51*c*, 51*d*, and 51*e* are driven later, they transmit the ultrasonic waves later. In the present embodiment, the driving pulses are input with delay times as shown in FIG. 6.

The later an element is in the order of 51*b*, 51*c*, 51*d*, and 51*e*, the higher the frequency of the ultrasonic wave transmitted from the element. Specifically, the cells that respectively constitute the elements 51*a*-51*e* have different membrane widths W, and thereby the different frequencies are realized (see equation (1)). It should be noted that the frequency may be changed by changing the thickness of the membrane on the basis of the principle expressed by equation (1) above.

Figure 9:
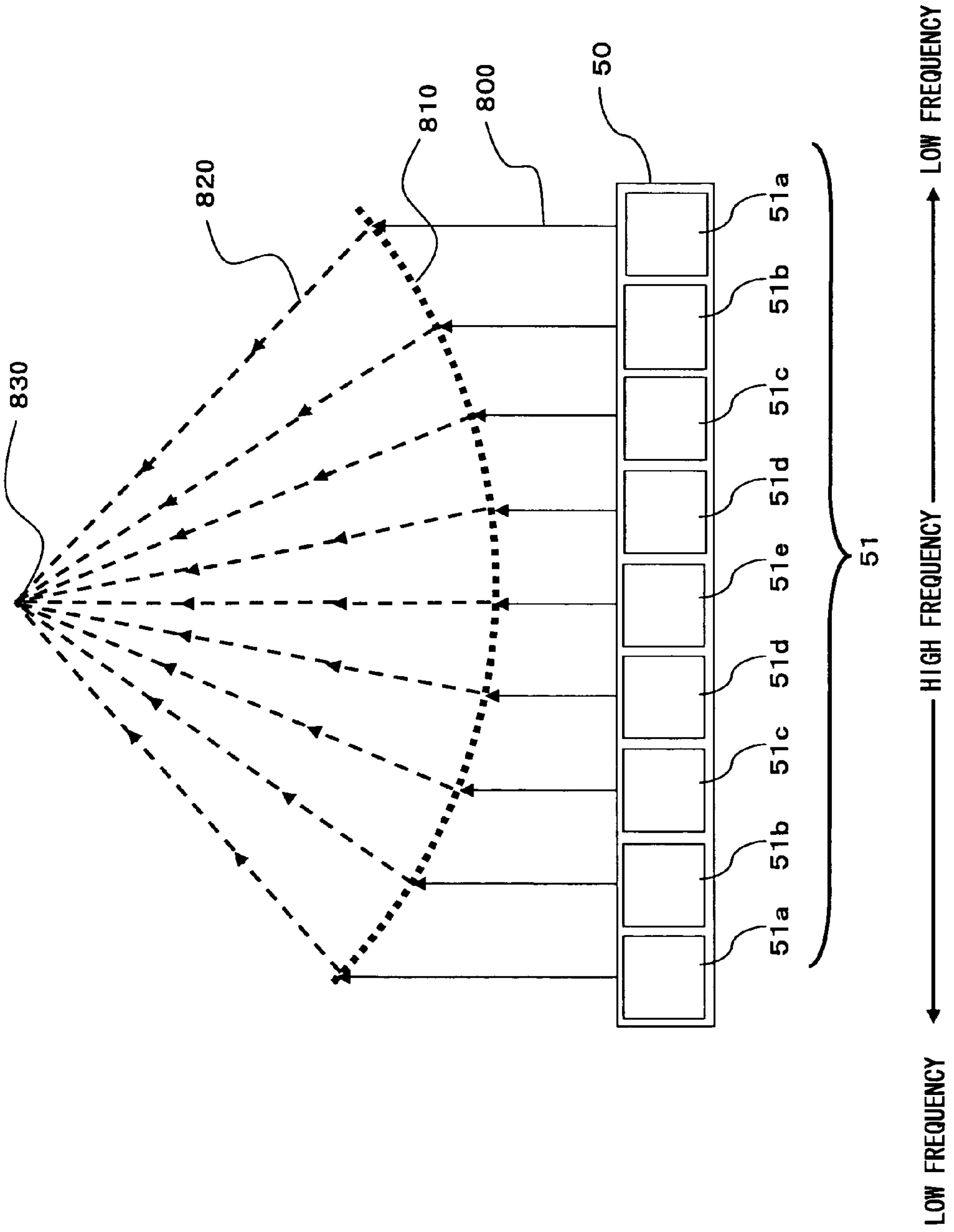
FIG. 9 shows a wavefront of synthesized ultrasonic waves in the third embodiment.

FIG. 9 shows a wavefront 810 of the synthesized ultrasonic waves according to the present embodiment. By controlling the timing at which the driving pulses are input into the transducer elements 51*a*, 51*b*, 51*c*, 51*d*, and 51*e*, it is possible to scan focal positions of the ultrasonic waves by using an electronic scanning method. When timing at which a driving pulse is applied to each transducer element is relatively delayed, as shown in FIG. 6, the wavefront 810 of the synthesized ultrasonic waves is realized, and the ultrasonic beams are converged at the position corresponding to the set delay times. Thereby, the same effect as that realized in the first embodiment can be realized.

Also, by changing the delay times, the wavefront of the synthesized waves can be changed and thereby the shape of the arc of the wavefront will also be changed. Accordingly, the center point of the convergence (focal point) will be changed and thereby a sector scanning that enables scanning of arbitrary focal points will also be realized.

As described above, it is possible to achieve the same effect as that achieved in the first embodiment by shifting the timing at which the driving pulses are applied to the elements (by providing a phase difference to the timing of inputting the driving pulses). An ultrasonic image at a relatively high resolution can be achieved from near portions to far portions by the configuration in which the central spot of the element transmits the ultrasonic wave at a high frequency, and the closer to the ends of the elements a spot is, the lower the frequency of the ultrasonic wave transmitted from the spot. Further, the function that has been conventionally realized by the plano-concave configuration can be realized easily.

Also, it is not necessary to curve the element, and the same function is realized by only control of the driving pulses; accordingly, the present embodiment is advantageous in manufacturing cost.

Fourth Embodiment

In the present embodiment, a capacitive micromachined ultrasonic transducer is explained in which two types of sound sources that respectively transmit ultrasonic waves at different frequencies are arranged alternately.

FIG. 10 shows a driving unit of the C-MUT according to the present embodiment. First, a flexible printed circuit (FPC) 118 is arranged on the surface of a membrane of an element 101, and a lower face electrode 119 is arranged on the surface of an insulating layer. A driving unit 117 is a device for driving the c-MUT 1, and includes ground wiring 117*a*, signal wiring 117*b*, grounds 117*c*, 117*g*, and 117*h*, a DC bias power source 117*d*, an RF power source 117*e*, and DC blocking capacitors 117*f* and 117*i*.

An upper electrode 107 is grounded at the ground 117*c* via the ground wiring 117*a*. The signal wiring 117*b* is for transmitting driving signals generated by the driving unit 117 to the c-MUT 101.

The RF power source 117*e* is an alternating current source for generating the driving signals. To generate the driving signals, not only alternating voltage components ($V_{rf}$) supplied from the RF power source 117*e*, but also direct voltage components ($V_{bias}$) supplied from the DC bias power source 117*d* are necessary. The driving signals thus generated are transmitted to the lower face electrode 119 via the DC blocking capacitor 117*f* and the signal wiring 117*b*. One terminal of the DC bias power source 117*d* is grounded at the ground 117*g*, and one terminal of the RF power source 117*e* is grounded at the ground 117*h*.

The DC blocking capacitors 117*f* and 117*i* are for preventing direct current of the DC bias power source 117*d* from flowing into a charge amplifier or into the RF power source 117*e*.

When the driving unit 117 is driven, the driving signal is transmitted to the c-MUT, and the membrane of each cell oscillates such that an ultrasonic wave is transmitted from each cell.

The basic configuration of the c-MUT 101 has been explained above. Next, a capacitive micromachined ultrasonic transducer using a parametric array according to the present embodiment will be explained.

Figure 11:
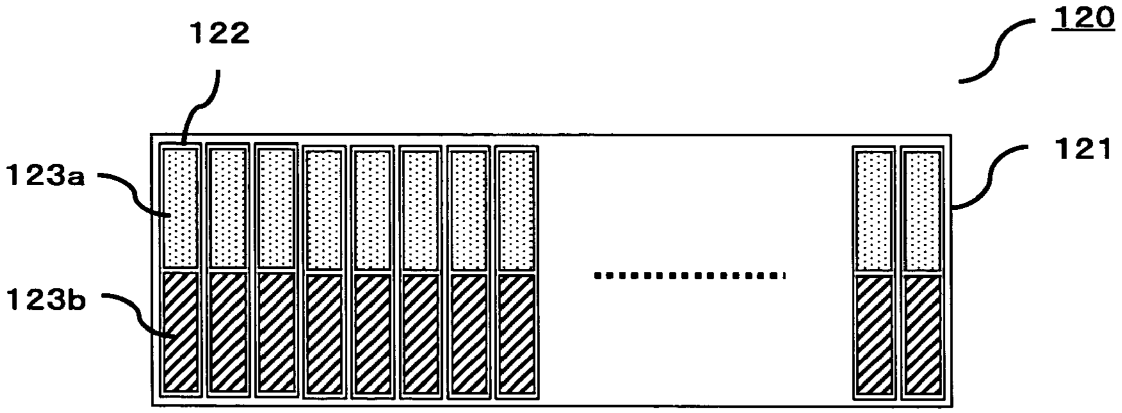
FIG. 11 shows a unit of a capacitive micromachined ultrasonic transducer according to the fourth embodiment.

FIG. 11 shows a unit of the capacitive micromachined ultrasonic transducer according to the present embodiment. A unit 120 of a silicon capacitive micromachined ultrasonic transducer is a unit of configuration in which a plurality of elements 122 are arranged on a silicon substrate 121. Each element 122 includes two transducer subelements (simply referred to as sub element hereinafter) 123*a* and 123*b*. The element explained in FIG. 1 corresponds to the subelement 123 in FIG. 11.

FIG. 12 shows the element and the subelement of the capacitive micromachined ultrasonic transducer according to the present embodiment. As described above, the element 122 includes two subelements 123 (123*a* and 123*b*). The subelements 123*a* and 123*b* respectively transmit ultrasonic waves at frequencies different from each other.

FIG. 13 is an enlarged view of a part (part 124 enclosed by a dashed line) of the subelement 123. The subelement 123 includes a plurality of cells 127. The cells 127 have the same configuration and thus transmit ultrasonic waves at the same frequency. An upper electrode 125 is arranged at the central point of the top surface of each cell 127. The upper electrode 125 on each cell is connected to the upper electrodes 125 on its adjacent cells via an interconnect electrode 126.

FIG. 14 shows a cross section across the line A1-A2 of the subelement 123 shown in FIG. 13. In FIG. 14, the cross section of the subelement 123 mainly consists of an insulation film 134, membranes 135 (the membranes 135 include an upper electrode 132), membrane supporting parts 133, lower electrodes 136, a silicon substrate 130, and cavities 131. A detailed explanation of the constituent components in FIG. 14 is omitted because they are explained in FIG. 1 and FIG. 2.

Each membrane 135 includes the upper electrode 132 and a membrane bottom film (the membrane 135 may further include a highly dielectric material layer). The upper electrode 132 includes the upper electrodes 125 and interconnect electrodes 126 on the above respective cells 127. The width of the cavity 131 (membrane width in each cell) is represented by W. The functions of these units are the same as those of the units explained in FIG. 1 and FIG. 2.

Figure 15A:
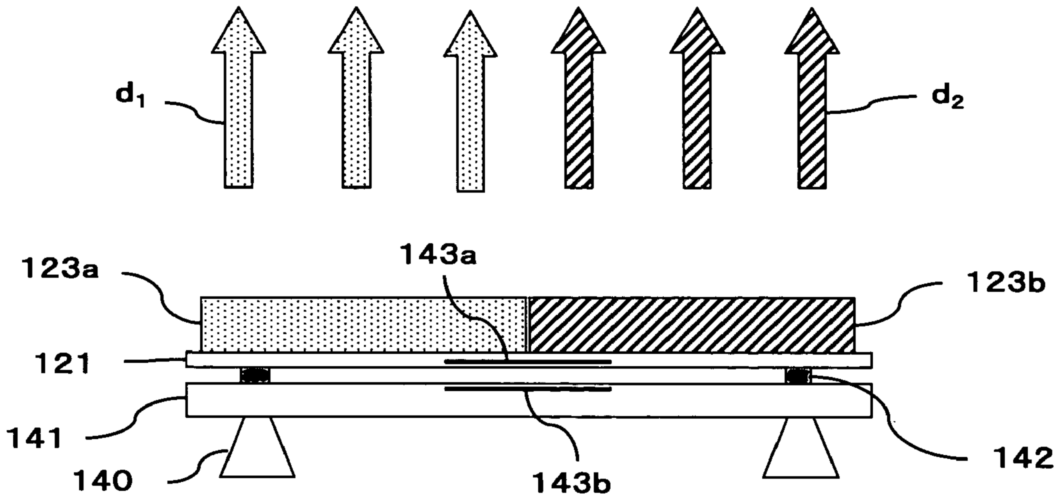
FIGS. 15A-15B show side views of a unit 120 according to the fourth embodiment (the unit 120 is viewed from the right or from the left) and transmission/reception of ultrasonic waves.
Figure 15B:
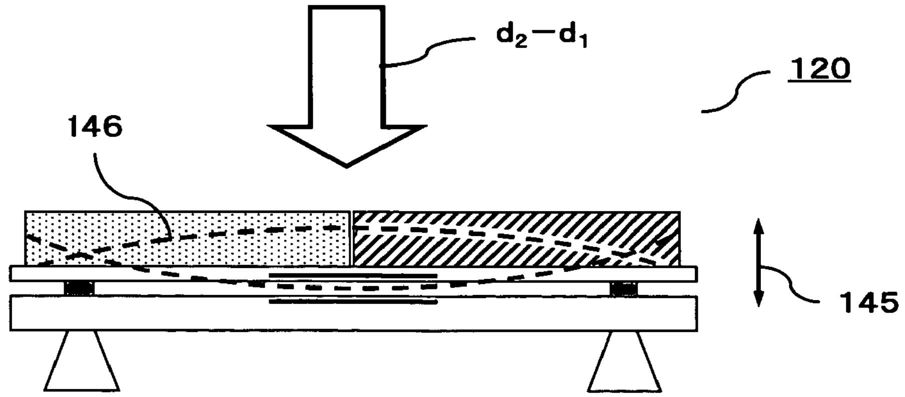

FIGS. 15A-15B show side views of the unit 120 according to the present embodiment (the side views of the unit 120 in FIG. 11 viewed from right or from left) and the transmission/reception of ultrasonic waves. FIG. 15A shows the transmission, and FIG. 15B shows the reception. In FIGS. 15A and 15B, the unit 120 includes the subelements 123*a* and 123*b*, the silicon substrate 121, bending oscillation supporting spacers 142, a second silicon substrate 141, second silicon substrate supporting parts 140, and electrodes 143*a* and 143*b*.

The subelements 123*a* and 123*b* are supported by the silicon substrate 121. Between the silicon substrate 121 and the second silicon substrate 141, the bending oscillation supporting spacers 142 are provided for securing a space in a prescribed volume. The silicon substrate 121 has an electrode 143*a* on its surface that faces the second silicon substrate 141, and the second silicon substrate 141 has an electrode 143*b* on its surface that faces the silicon substrate 121.

In FIG. 15A, the subelements 123*a* and 123*b* respectively transmit ultrasonic waves at different frequencies $d_1$ and $d_2$. In the present embodiment, it is assumed that $d_1<d_2$ is satisfied. It is also assumed that the ultrasonic wave whose frequency component is $d_1$ is transmitted from the subelement 123*a*, and the ultrasonic wave whose frequency component is $d_2$ is transmitted from the subelement 123*b*. In this configuration, ultrasonic waves are transmitted from each cell 127 in the respective subelements 123. By changing the membrane width W of each cell, it is possible to transmit ultrasonic waves at different frequencies on the basis of the principle expressed by equation (1). The emission of the ultrasonic waves at different frequencies is also realized by changing the membrane thickness tm.

When the ultrasonic waves having the frequency components $d_1$ and $d_2$ are transmitted in the same direction, a difference tone (difference frequency signal $d_2-d_1$) is generated. The difference tone is at a low frequency, such that it sufficiently propagates over a long distance. Also, as an acoustic characteristic, a difference tone has a beam pattern sharper than that of an ultrasonic wave at the same frequency, such that spatial directivity is improved and spatial resolution is also improved (usually, a beam pattern spreads greatly at a low frequency, and the spatial resolution deteriorates). Also, because a side robe does not appear in the analysis range, it is possible to suppress ultrasonic image noise, thereby improving the quality of an ultrasonic image.

FIG. 15B shows the reception of the reflected wave of the difference frequency signal $d_2-d_1$ that was generated in FIG. 15A and was reflected in the body cavity. When receiving the wave, the element 123 and the silicon substrate 121 serve as a bending oscillator. Numeral 145 denotes a received ultrasonic wave oscillation, and numeral 146 denotes bending resonance caused by the received ultrasonic wave oscillation 145. Acoustic pressure is applied to the entire surface of the element 123, and the received ultrasonic wave oscillation 145 occurs over the entirety of the element 123.

Next, the received ultrasonic wave oscillation 145 causes the bending resonance 146 in the element 123 and the silicon substrate 121. Specifically, the distance between the electrodes 143*a* and 143*b* arranged such that they face each other is changed by the bending deformation, the inter electrode capacitance is changed, and the reception voltage is changed. On the basis of this voltage change, an echo image is formed.

The silicon substrate is a film that is sufficiently thin so as to be able to undergo the bending oscillation Even if the thickness of the membrane is several μm, the depth of the cavity is generally the same, and the thickness of the Si substrate is 50 μm, the total thickness will be equal to or smaller than 60 μm. This level of thickness allows bending deformation on a large scale.

Because the ultrasonic wave is transmitted element by element, the subelements constituting each element are simultaneously driven. Specifically, the subelements in the elevation direction, i.e., the direction orthogonal to the scanning direction (for example, the direction of scanning from right to left), are simultaneously driven. Also, by conducting the driving in units of elements, linear scanning and sector scanning can be performed. Also, the areas that respectively transmit high-frequency waves and low-frequency waves are configured to be of the same size in one unit. When a virtual center line is drawn in the elevation direction, the subelements are arranged on both sides of the virtual center line.

Because the element 123 and the silicon substrate 121 serve as the bending oscillator, and the bending oscillation supporting spacers 142 serve as the nodes of the oscillation as shown in FIG. 15B, it is possible to adjust a resonant frequency characteristic of this bending oscillator by adjusting the positions of the bending oscillation supporting spacers 142. Specifically, by adjusting the positions of the bending oscillation supporting spacers 142 in accordance with the frequency of the difference tone generated, an appropriate oscillation amplitude is realized, such that the sensitivity of an echo image is enhanced. In the present embodiment, a high-frequency wave is an ultrasonic wave at a frequency that is relatively higher than the frequencies of other ultrasonic waves (low frequency), and a low-frequency wave is an ultrasonic wave at a frequency that is relatively lower than the frequencies of other ultrasonic waves (high frequency).

The reason that the parametric sound is used in the ultrasonic diagnosis is that a low-frequency difference tone propagates over a long distance as its general characteristic and also that the ultrasonic beam width is small, which is a characteristic that results from a non-linear effect. Accordingly, it is necessary to generate a difference signal of a low frequency (parametric signal) from two signals having frequency components that are close to each other (on the order of several MHz).

It is desirable that the frequency of the difference signal of the above two signals having the frequency components that are a distance from each other on the order of several MHz be one-tenth of the original frequency. If the frequency is lower than the above value, the resolution deteriorates very much, and if the frequency is higher than the above value, the ultrasonic wave propagates over a shorter distance. However, this condition of the value is not an absolute condition, and in some prior art, the condition of $f_0=f_2-f_1=f_1(f_2=2f_1)$ is employed (see, for example, Japanese Patent Application Publication No. 8-80300).

As described above, in an ultrasonic transducer using a parametric array, it is possible to reduce the size of a transducer by using a capacitive micromachined ultrasonic transducer.

Fifth Embodiment

In the present embodiment, a capacitive micromachined ultrasonic transducer that achieves a parametric effect that is greater than that achieved in the fourth embodiment will be explained.

FIG. 16 shows the first example of a unit 150 of the capacitive micromachined ultrasonic transducer according to the present embodiment. In FIG. 11, the adjacent elements are arrayed in the same direction; however, in FIG. 16, the adjacent elements 123 are arrayed in opposite directions. By alternately arraying the elements 123 that respectively transmit the ultrasonic waves at the two frequencies as described above, the two frequency components can be mixed easily, such that a greater parametric effect can be achieved.

Figure 17:
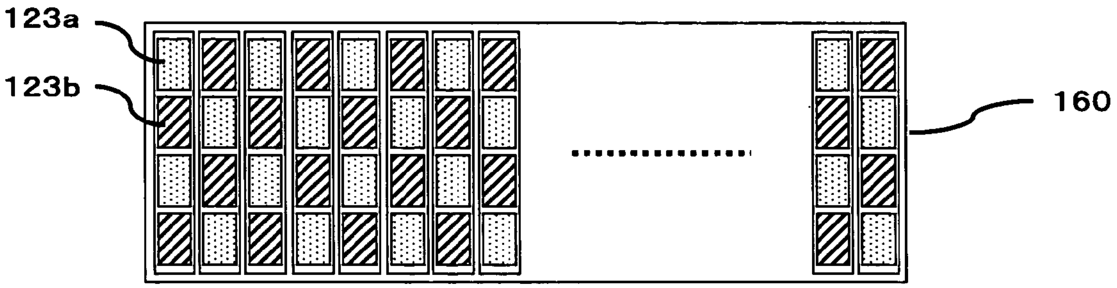
FIG. 17 shows the second example of the unit 140 of the capacitive micromachined ultrasonic transducer according to the fifth embodiment.

FIG. 17 shows the second example of a unit 160 of the capacitive ultrasonic transducer according to the present embodiment. In FIG. 17, each element includes four subelements 123 that can be categorized into two types (the subelements 123*a* and 123*b* are alternately arrayed). Also, between the adjacent elements, the subelements 123*a* and 123*b* are alternately arrayed. With this array method, the two frequency components can be mixed more easily than in the configuration shown in FIG. 16. Also, by further dividing the subelements and by arraying them such that their directions alternate, further greater parametric effect can be achieved.

In FIG. 16 and in FIG. 17, the areas that respectively transmit ultrasonic waves with high frequency and low frequency are configured to be of the same size. Also, It should be noted that the shapes of the subelements are not limited to being rectangular, and may be, for example, square, circular, or hexagonal, even though the subelements are rectangular in the present embodiment.

Sixth Embodiment

In the present embodiment, a capacitive micromachined ultrasonic transducer will be explained in which the aperture is circular and cells respectively having two resonant frequencies that are close to each other are alternately arranged in concentric circles such that the two elements are of the same size.

Figure 18A:
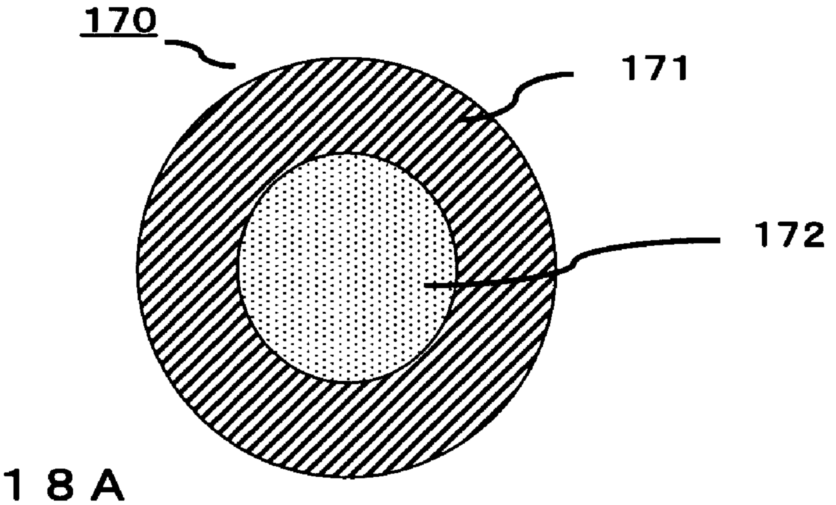
FIGS. 18A-18C show a capacitive micromachined ultrasonic transducer according to the sixth embodiment.
Figure 18B:
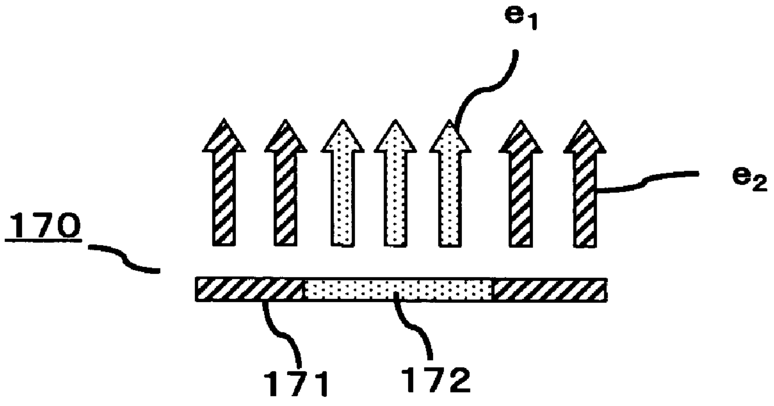
Figure 18C:
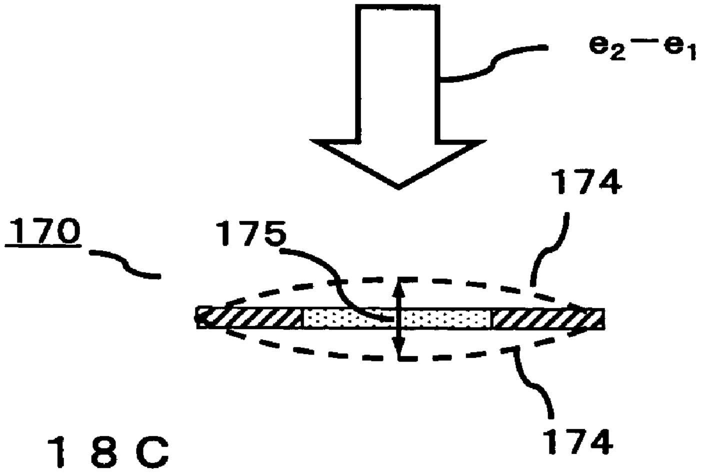

FIG. 18A-18C shows the capacitive micromachined ultrasonic transducer according to the present embodiment. FIG. 18A is a top view of a capacitive micromachined ultrasonic transducer 170. FIG. 18B is a lateral view thereof (when transmitting ultrasonic waves). FIG. 18C is another lateral view (when receiving ultrasonic waves). In FIG. 18A, the capacitive micromachined ultrasonic transducer 170 includes two elements, i.e., an element 172 that transmits an ultrasonic wave having high-frequency components and an element 171 that transmits an ultrasonic wave having low-frequency components.

In FIG. 18B, the elements 171 and 172 respectively transmit ultrasonic waves at different frequencies $e_1$ and $e_2$. In the present embodiment, it is assumed that the relationship $e_1<e_2$ is satisfied. The element 172 transmits the ultrasonic wave at the frequency $e_1$ and the element 171 transmits the ultrasonic wave at the frequency $e_2$. The ultrasonic wave is transmitted from each cell in the elements. By changing the membrane width W in each cell, it is possible to transmit the ultrasonic waves at different frequencies on the basis of the above equation (1). The ultrasonic waves at different frequencies can also be transmitted by changing the thickness tm of the membrane.

When the ultrasonic waves having different frequency components $e_1$ and $e_2$ are transmitted in the same direction, the difference tone (difference frequency signal $e_2-e_1$) is thereby generated as described in the fourth embodiment. The difference tone is at a low frequency, such that it sufficiently propagates over a long distance. Also, regarding its acoustic characteristics, a difference tone has a beam pattern sharper than that of an ultrasonic wave at the same frequency such that spatial directivity and spatial resolution are improved (usually, a beam pattern spreads at a low frequency, and the spatial resolution deteriorates). Also, because a side robe does not appear in the analysis range, it is possible to suppress the noise of an ultrasonic image, and thereby the quality of an ultrasonic image can be improved.

FIG. 18C shows the reception of a reflected wave of the difference frequency signal $e_2-e_1$ that was generated in FIG. 18B and that was reflected in a body cavity. When receiving waves, the unit 170 serves as a bending oscillator. Numeral 175 denotes a received ultrasonic wave oscillation, and numeral 174 denotes a bending resonance caused by the received ultrasonic wave oscillation 175. An acoustic pressure is applied to the entire surface of the unit, and the received ultrasonic wave oscillation 175 occurs in the unit 170. Then, the unit 170 causes the bending resonance 174 and absorbs the received ultrasonic wave oscillation 175. Then, the received ultrasonic wave oscillation 175 is converted into electric signals. It should be noted that the configuration shown in FIG. 18A-18C includes, similarly to that shown in FIG. 15A-15B, the subelements, the silicon substrate, the supporting spacers, the second silicon substrate, the second silicon substrate supporting parts, and electrodes; however, these members are not shown in FIG. 18A-18C.

Additionally, the c-MUT is driven on the basis of each unit. Accordingly, the elements 171 and 172 constituting the unit are simultaneously driven, and a drive control is performed by using a plurality of the units. Thereby, it is possible to perform the linear scanning or the sector scanning. Also, the areas that respectively transmit the high-frequency wave and the low-frequency wave are configured to be of the same size. Also, both of the two elements, i.e., the element 172 that transmits the ultrasonic wave having the high-frequency components and the element 171 that transmits the ultrasonic wave having the low-frequency components, are used in FIG. 18A-18C; however, the configuration is also possible in which these elements are alternatively arrayed in concentric circles as several layers.

Seventh Embodiment

In the present embodiment, a capacitive micromachined ultrasonic transducer that generates an ultrasonic wave by synthesizing and converging a plurality of difference tones generated by using the parametric array will be explained.

Figure 19:
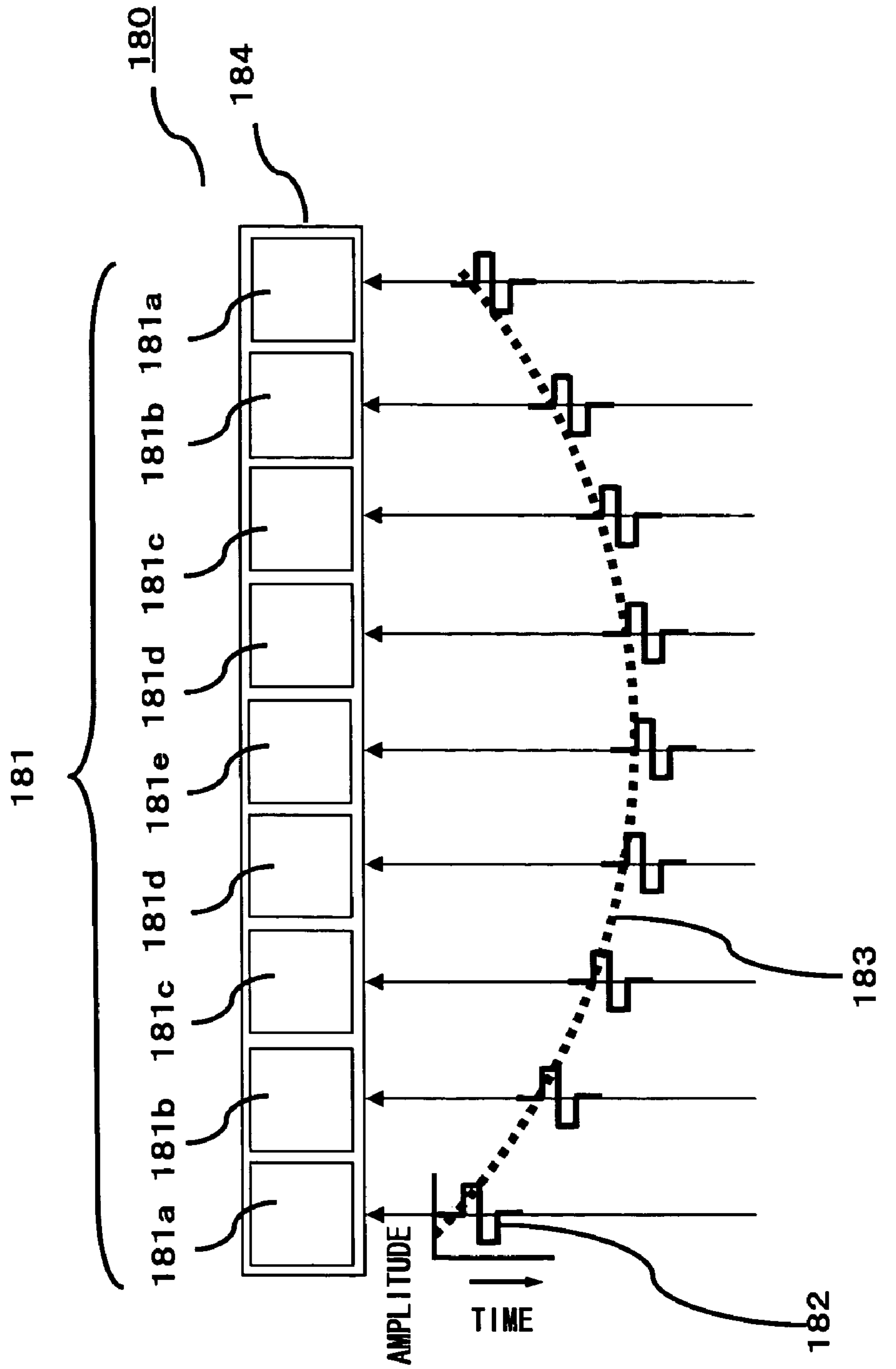
FIG. 19 shows the timing of inputting driving pulses into a unit and respective elements of a capacitive micromachined ultrasonic transducer in the seventh embodiment.

FIG. 19 shows a unit of the capacitive micromachined ultrasonic transducer according to the present embodiment. On a substrate 184, a plurality of elements 181 (nine elements, 181*a*, 181*b*, 181*c*, 181*d*, 181*e*, 181*d*, 181*c*, 181*b*, and 181*a*) are arranged. In this embodiment, this group of elements 181 is referred to as a unit 180.

Figure 20:
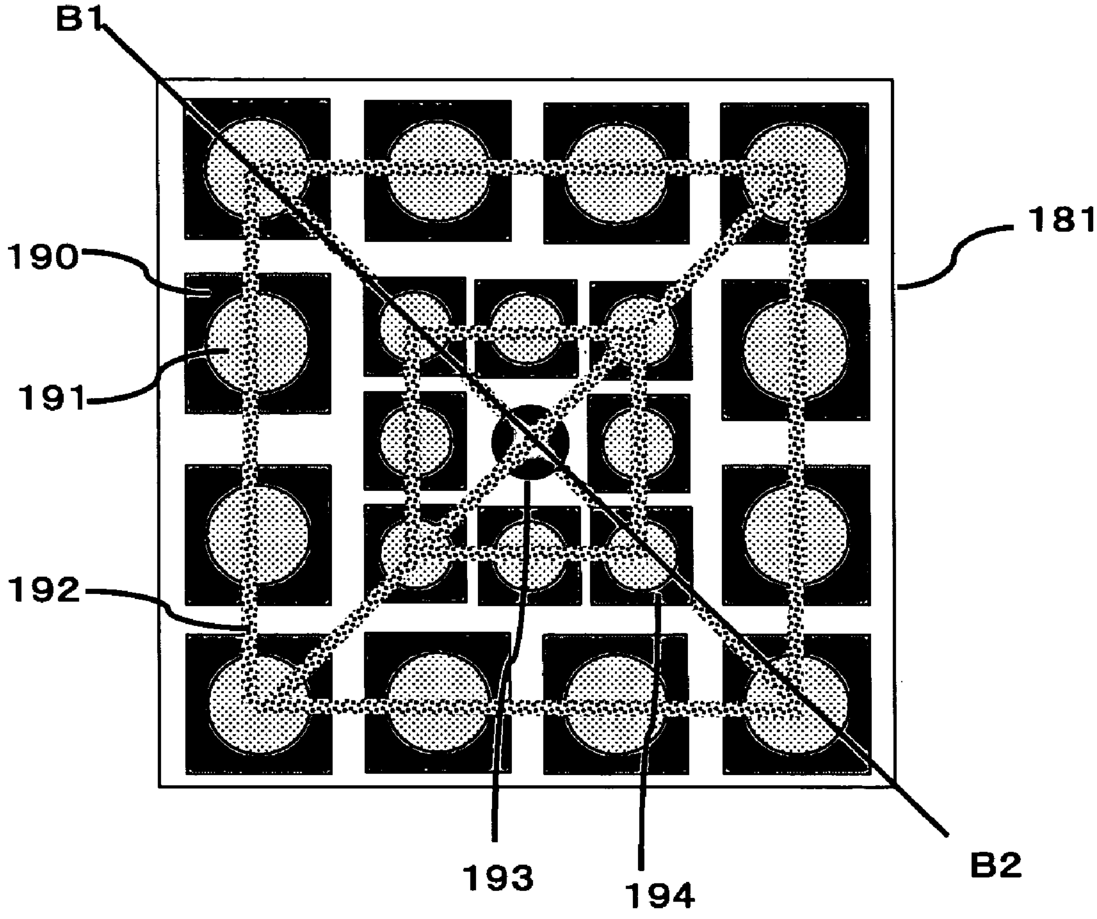
FIG. 20 shows the upper face of an element 151 according to the seventh embodiment.

FIG. 20 shows an upper face of the element 181 according to the present embodiment. In the element 181, square cells 190 are formed along the periphery and square cells 194 are formed in the inner space. As shown in FIG. 20, cells 190 are larger than cells 194; accordingly, cells 190 transmit ultrasonic waves having low-frequency components and cells 194 transmit ultrasonic waves having high-frequency components on the basis of the principle expressed by equation (1).

The only difference between cells 191 and cells 194 is the size, and they have the same configuration. At the central point of the top surface of both cells 191 and cells 194, an upper electrode 191 is provided. The upper electrode 191 on each cell is connected to the cells 191 on its adjacent cells via an interconnect electrode 192. Also, an interconnect via hole 193 is formed at the central point of the element 181.

Figure 21:
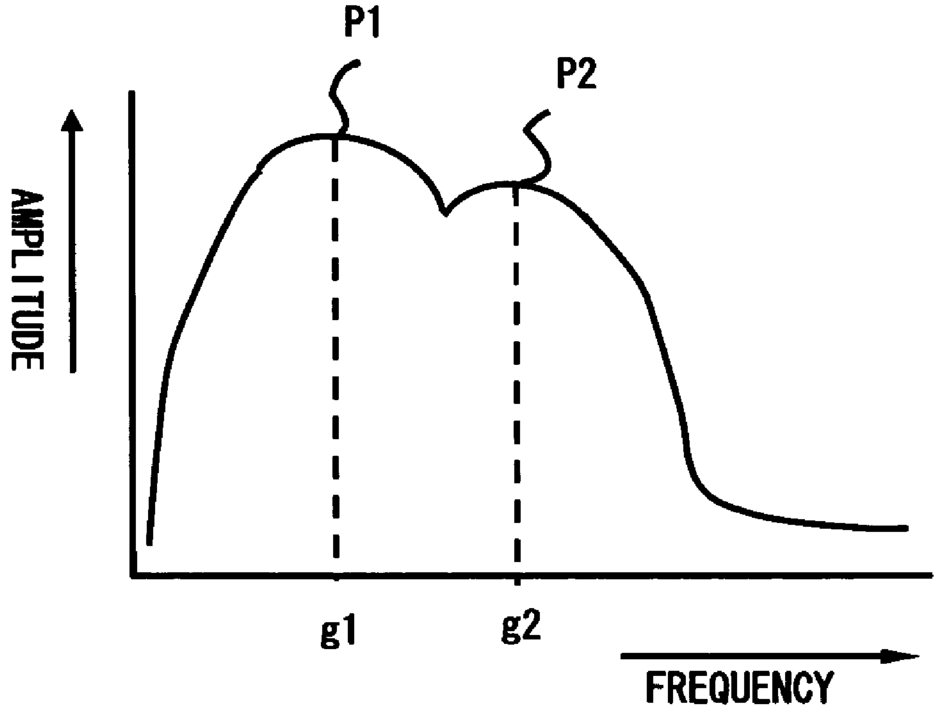
FIG. 21 shows the frequency components of a wave transmitted by an element 181.

FIG. 21 shows the frequency components transmitted by the element 181. The graph shown in FIG. 21 includes two amplitude peaks P1 and P2. The frequency at the peak P1 is g1 (g1<g2) and is of the ultrasonic wave transmitted from the cell 190. The frequency at the peak P2 is g2 (g2>g1) and is of the ultrasonic wave transmitted from the cell 194.

Figure 22:
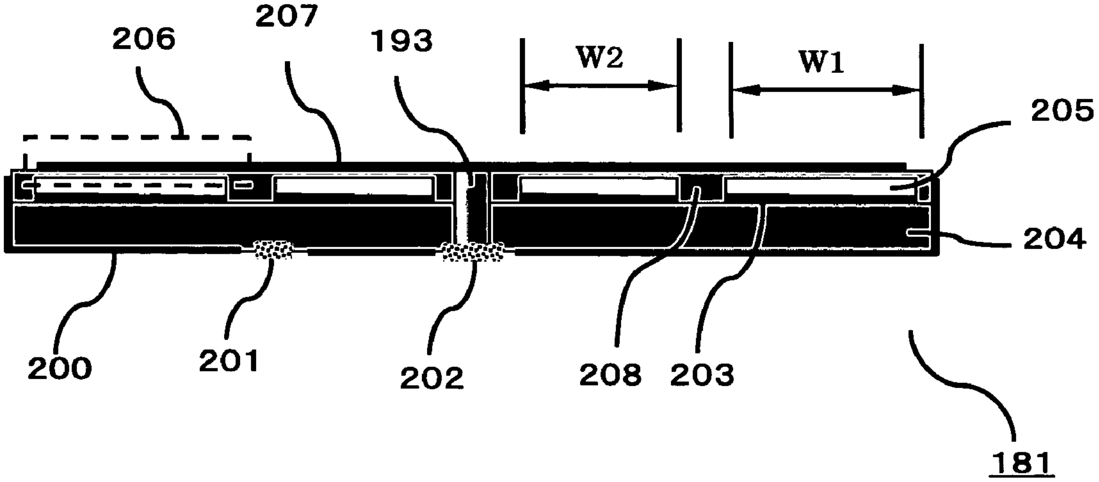
FIG. 22 shows a cross section of the element shown in FIG. 20 across the line A1-A2.

FIG. 22 shows a cross section of the element 181 shown in FIG. 20 across the line B1-B2. In FIG. 22, the cross section of the element 181 includes an insulation film 200, contact pad electrodes 201 and 202, lower electrodes 203, a silicon substrate 204, cavities 205, a membrane 206, an upper electrode 207, and membrane supporting parts 208.

The membrane 206 includes an upper electrode 207 and a membrane bottom film (highly dielectric material may be included further). The upper electrode 207 includes an upper electrode 191 on each cell and an interconnect electrode 192. The membrane supporting parts 208 are for supporting the membrane 206 and are made of highly insulative material such as SiN, $SiO_2$ or the like. The width of the cavity 205 (the width of the electrode in units of cells) is represented by W. The functions of these members are the same as those in the fourth embodiment.

The membrane width of cell 190 is represented by W1, and the membrane width of cell 194 is represented by W2. They satisfy the relationship of W1>W2. In the element 180, cells 190 and cells 194 are configured such that they have generally the same total size (in FIG. 20, the cells 190 and the cells 194 are not of the same size for convenience of explanation).

By configuring the elements as above, ultrasonic waves at a high frequency and ultrasonic waves at a low frequency are transmitted in the same direction. Accordingly, the difference tone is generated between them and the parametric effect is achieved.

The operations of the unit 180 that are realized in the present embodiment will be explained by once again referring to FIG. 19. First, the driving pulses denoted by unit 180 are input into the respective elements. In FIG. 19, the pulses 182 represent the amplitudes with respect to the time. A delay time is given to the driving pulse input into each element, and these driving pulses are input in the order of 181*a*, 181*b*, 181*c*, 181*d*, and 181*e* at prescribed intervals. Also, each element includes the driving unit explained in FIG. 10, and the driving pulse is input into this driving unit. The driving pulse is transmitted from a control unit in an ultrasonic endoscope apparatus (not shown).

By inputting the driving pulses to the element using delay times, the ultrasonic waves are transmitted from the element with time gaps. Specifically, the element 181*a* that is driven earlier transmits the ultrasonic wave earlier, and because the elements 181*b*, 181*c*, 181*d*, and 181*e* are driven later, they transmit the ultrasonic waves later.

Figure 23:
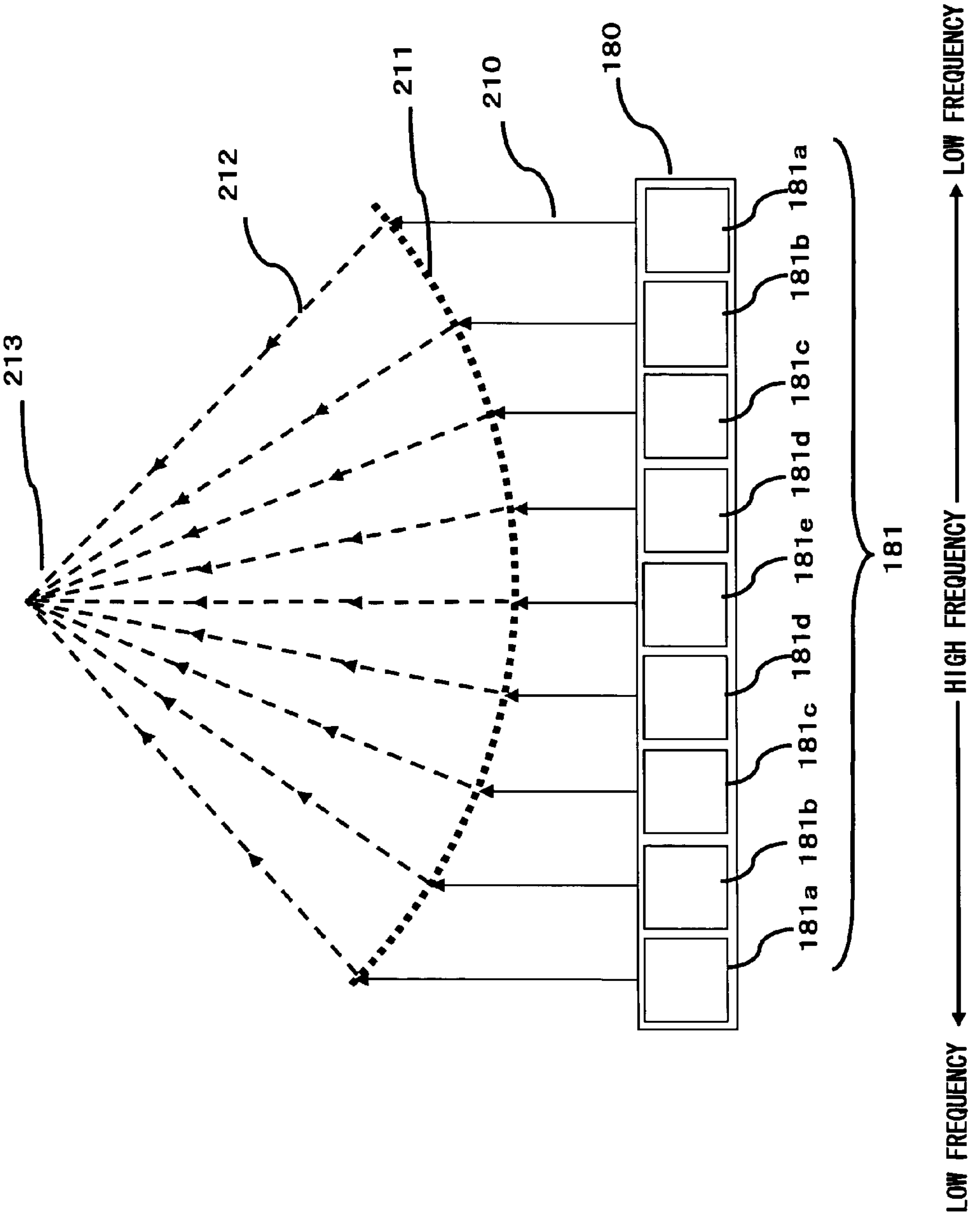
FIG. 23 shows a wavefront of synthesized ultrasonic waves according to the seventh embodiment.

FIG. 23 shows a wavefront 181 of the synthesized ultrasonic waves according to the present embodiment. By controlling the timing at which the driving pulses are input into the transducer elements 181*a*, 181*b*, 181*c*, 181*d*, and 181*e*, it is possible to synthesize wavefronts of ultrasonic waves using an electronic scanning method. As explained in FIG. 19, by delaying the driving pulses such that the delayed pulses present an arc, the wavefronts of ultrasonic waves 210 interfere with each other, and the wavefront becomes concave (shown as a synthesized wavefront 211) such that it is possible to control the ultrasonic beams that are converged at an arbitrary position. Then, a wavefront 211 is created whose entire shape is an arc shape. When such a wavefront is created, the synthesized ultrasonic waves 212 are converged at a center point 213 with the arc as the focal point. Thereby, the same effect as that of the fourth embodiment can be achieved.

Also, by changing the delay times, the wavefront of the synthesized waves can be changed; thereby, the shape of the arc of the wavefront will also be changed. Accordingly, the center point of the convergence (focal point) will also be changed, and thereby sector scanning that enables scanning of arbitrary focal points will also be realized.

As described above, by delaying the driving pulses such that they present a parabolic shape, it is possible to synthesize and converge the ultrasonic waves transmitted from the respective elements, and sector scanning is realized. Also, because the ultrasonic waves transmitted from the respective elements are difference tones obtained by using the parametric array, spatial resolution and ultrasonic image quality higher than those realized by the conventional sector scanning are realized.

Eighth Embodiment

In the present embodiment, the case will be explained in which at least three subelements having different and adjacent resonant frequencies are used.

Figure 24:
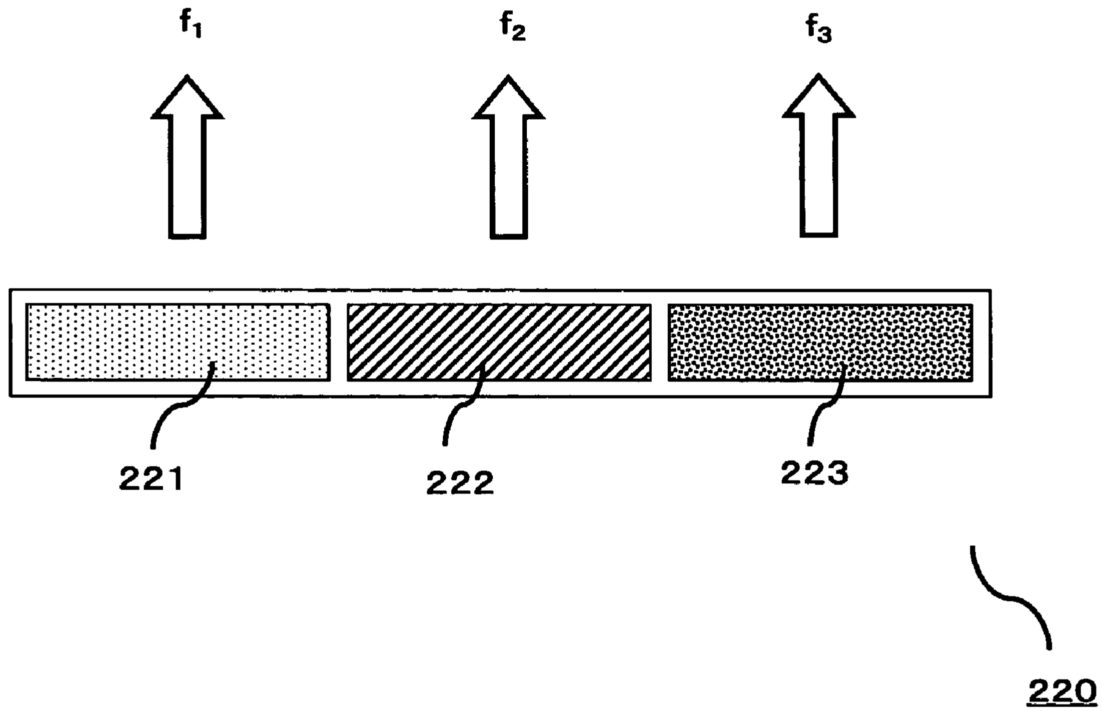
FIG. 24 shows an element according to the eighth embodiment.

FIG. 24 shows an element 220 in the present embodiment. In FIG. 24, three subelements 221, 222, and 223 are shown. Subelement 221 transmits an ultrasonic wave at the frequency $f_1$. Subelement 222 transmits an ultrasonic wave at the frequency $f_2$. Subelement 223 transmits an ultrasonic wave at the frequency $f_3$. These frequencies satisfy the relationship of $f_1<f_2<f_3$.

In this case, three types of difference frequency signals, $f_2-f_1$, $f_3-f_2$, and $f_3-f_1$, are generated, and thus a difference frequency signal having a wide bandwidth is generated. Because these three types of signals respectively have different bandwidths, the bandwidth becomes wider even though all of them are parametric signals. After a inverse Fourier transformation is performed on the parametric signal having the above characteristic, the pulse width with respect to the time axis becomes shorter. The fact that the time pulse width becomes shorter supports the fact that the resolution in the depth direction is improved.

In the fourth embodiment, the ultrasonic wave having the frequency component $d_1$ and the ultrasonic wave having the frequency component $d_2$ are used for generating in the target object the parametric signal having the frequency component $d_2-d_1$ in the configuration shown in FIG. 15A-15B, and the bending oscillator having the resonant frequency in the frequency component $d_2-d_1$ receives the echo signal of the parametric signal. If there is only one difference frequency signal $d_2-d_1$, this configuration functions sufficiently. However, in the case when the transmission signals have the frequencies $f_1$, $f_2$, and $f_3$ as in the present embodiment, three types of difference frequency signals, $f_2-f_1$, $f_3-f_2$, and $f_3-f_1$, are generated.

Accordingly, the detection of the received signal (reflected wave) has to correspond to these three types of frequencies. The two methods of reception will be explained below.

Figure 25A:
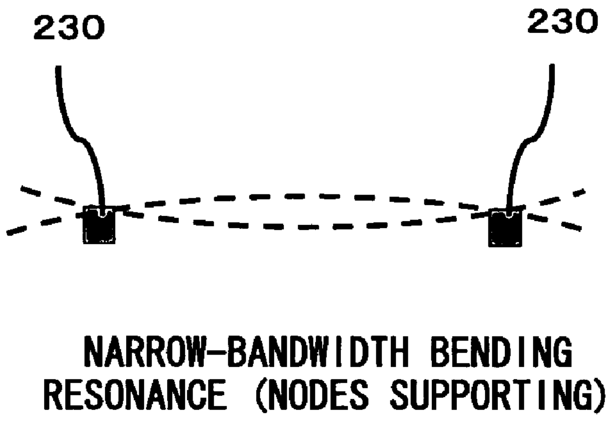
FIGS. 25A-25B show the first method of detecting a received signal according to the eighth embodiment.
Figure 25B:
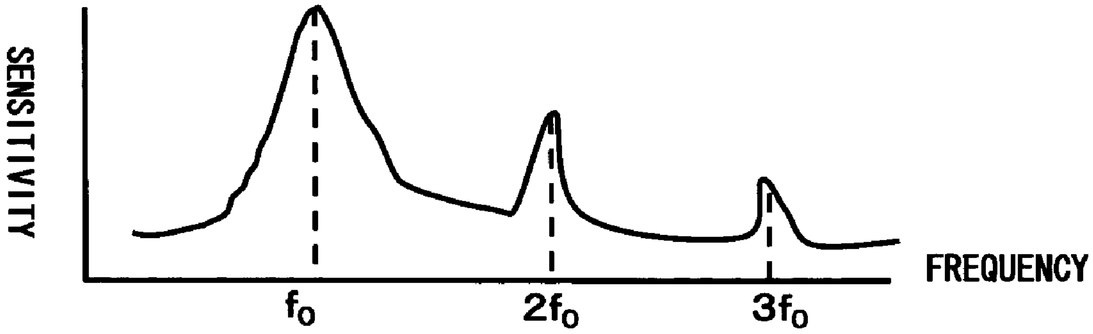

FIG. 25A-25B shows the first method of detection of the received signal according to the present embodiment. FIG. 25A shows the bending oscillation in the lateral direction of the element 220 which functions as the bending oscillator. In this configuration, the resonance has an overtone that is an integral multiple of the resonance but its response sensitivity is low. Accordingly, the frequencies $f_1$, $f_2$, and $f_3$ ($f_1<f_2<f_3$) are selected such that equations $f_3-f_2=2f$ and $f_3-f_1=3f_0$ are satisfied on the condition that $f_2-f_1=f_0$. The configuration for this case is basically the same as that shown in FIG. 15A-15B, in which the element is supported at nodes 230. Because of this configuration, bending resonance (narrow-bandwidth bending resonance) is caused at $f_0$, $2f_0$, and $3f_0$ as shown in FIG. 25B.

Figure 26A:
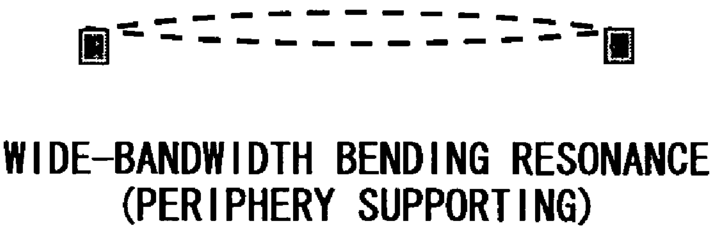
FIGS. 26A-26B show the second method of detecting the received signal according to the eighth embodiment.
Figure 26B:
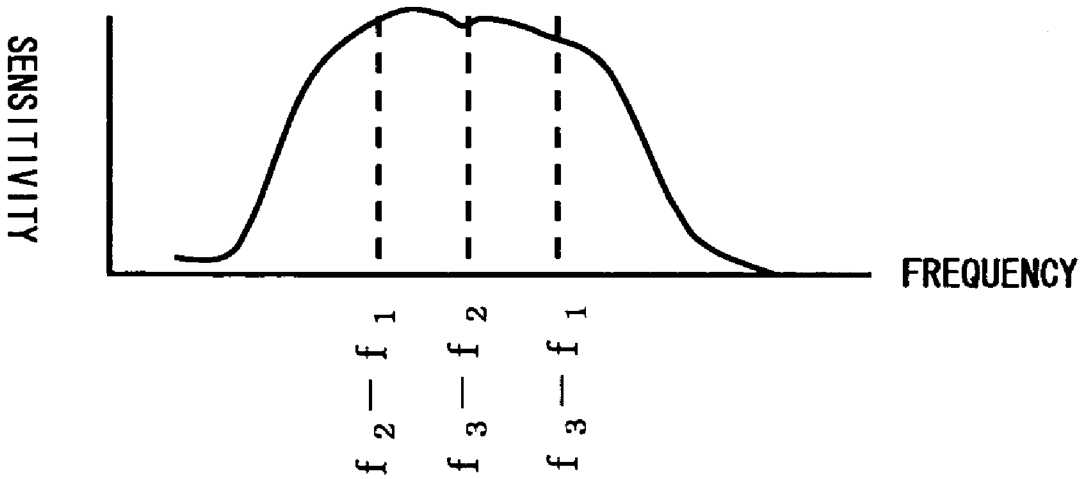

FIG. 26A-26B shows the second method of the detection of the received signal according to the present embodiment. FIG. 26A shows the bending oscillation in the lateral direction of the element 220 which functions as the bending oscillator. In the basic configuration as shown in FIG. 26A, wideband oscillations are caused by supporting the periphery of the element 220, and mechanical damping is forcibly applied to the bending resonance at the frequency $f_0$. Thereby, wide-bandwidth bending resonance at $f_2-f_1$, $f_3-f_2$, and $f_3-f_1$ is caused as shown in FIG. 26B.

Figure 27:
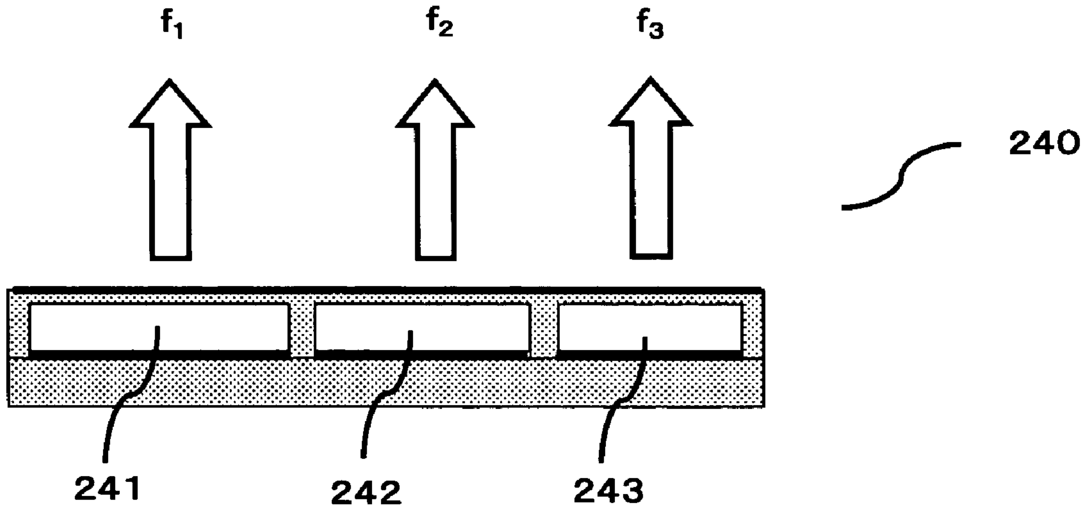
FIG. 27 shows an example of the case in which the eighth embodiment is realized in units of cells.

In the present embodiment, the three subelements having different and adjacent resonant frequencies are used; however, the scope of the present invention is not limited to this configuration, and cells 241, 242, and 243 (numeral 240 denotes an element) having different and adjacent resonant frequencies as shown in FIG. 27 can be used additionally. Also, it is desirable to arrange the three elements having different and adjacent resonant frequencies in descending or ascending order of frequencies; however, the scope of the present invention is not limited to this, and the elements may be arranged in a random order, depending on the application.

According to the present embodiment, it is possible to transmit and receive a plurality of types of parametric signals, i.e., it is possible to transmit and receive signals in a wide bandwidth.

As described above, it is possible to obtain an ultrasonic image of both shallow and deep sites at a high resolution by using the capacitive micromachined ultrasonic transducer.

In addition, by applying the present invention, it is possible to reduce the size of a capacitive micromachined ultrasonic transducer that has a parametric characteristic.

What is claimed is:

1. A capacitive micromachined ultrasonic transducer, comprising:

- a membrane having a first electrode and a supporting film supporting the first electrode;
- a second electrode arranged opposite to the supporting film;
- a membrane supporting part disposed between the membrane and the second electrode thereby forming a plurality of spaces between the membrane and the second electrode;
- a plurality of transducers cells, having the membrane, the spaces and the second electrode, arranged such that as a distance of each of the transducer cells to a periphery of the ultrasonic transducer decreases, the resonant frequency of each of the transducer cells decreases from a center of the transducer cells to a periphery of the transducer cells;
- a surface of the membrane on a side of the first electrode being curved in a recessed shape such that a plurality of ultrasonic beams transmitted from the surface of the membrane on the side of the first electrode are in focus;
- a flexible printed circuit joined to the surface of the membrane;
- a plurality of slits formed from a side of the second electrode to a side of the membrane supporting part; and
- a filling material filled into each of the plurality of slits for holding the recessed shape, the filling material maintaining the plurality of slits in a configuration where a width of each slit is larger on the side of the second electrode than on a side of the membrane.

2. The capacitive micromachined ultrasonic transducer according to claim 1, wherein:

the transducer cell is formed on a silicon substrate; and an electrical insulation film is formed on a surface of a side of the membrane that is opposite to the second electrode.

3. An ultrasonic endoscope apparatus, comprising: the capacitive micromachined ultrasonic transducer according to claim 1.

4. The capacitive micromachined ultrasonic transducer according to claim 1, wherein each of the slits extends to each of the membrane supporting parts.

* * * * *